(12) United States Patent
Eissenstat et al.

(10) Patent No.: US 8,673,970 B2
(45) Date of Patent: *Mar. 18, 2014

(54) HIV PROTEASE INHIBITOR AND CYTOCHROME P450 INHIBITOR COMBINATIONS

(75) Inventors: Michael Eissenstat, Frederick, MD (US); Dehui Duan, Frederick, MD (US); John W. Erickson, Potomac, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 302 days.

This patent is subject to a terminal disclaimer.

(21) Appl. No.: 12/919,011

(22) PCT Filed: Feb. 23, 2009

(86) PCT No.: PCT/US2009/034926
§ 371 (c)(1),
(2), (4) Date: Dec. 21, 2010

(87) PCT Pub. No.: WO2009/105782
PCT Pub. Date: Aug. 27, 2009

(65) Prior Publication Data
US 2011/0112137 A1   May 12, 2011

Related U.S. Application Data

(60) Provisional application No. 61/030,531, filed on Feb. 21, 2008.

(51) Int. Cl.
*A61K 31/36* (2006.01)
*A61K 31/34* (2006.01)

(52) U.S. Cl.
USPC .......................................... 514/465; 514/470

(58) Field of Classification Search
USPC .................................................. 514/465, 470
See application file for complete search history.

(56) References Cited

U.S. PATENT DOCUMENTS

| 8,048,871 B2 * | 11/2011 | Eissenstat et al. ............ 514/183 |
| 2005/0209301 A1 | 9/2005 | Eissenstat et al. |
| 2005/0267074 A1 | 12/2005 | Eissenstat et al. |

FOREIGN PATENT DOCUMENTS

| WO | WO 2005/110428 | * | 11/2005 |
| WO | WO 2008/022345 | | 2/2008 |
| WO | WO 2008/022345 A2 | * | 2/2008 |

OTHER PUBLICATIONS

Cannon J.G. "Analog Design" Burgers Medicinal Chemistry and Drug Discovery, Edition 5, vol. 1, Chapter 19, p. 783-802, 1995.*
Schafer et al. "Failure is an option: learning from unsuccessful proof-concept trials," Drug Discovery Today, 2008, vol. 13, No. 21/22 pp. 913-916.*
Horig et al. "From bench to clinical and back: perspective on the $1^{st}$ IQPC translation research conference" Journal of Translational Medicine, 2004, vol. 2, No. 44, p. 1-8.*
Monika et al: "Pharmacokinetics of darunavir/ritonavir and TMC125 alone and coadministered in HIVnegative volunteers", EPO Form 1703 01.91TRI Antiviral Therapy—An Official Publication of the International Society for Antiviral Research, MTM Publications, London, GB, val. 12, No. 5, Jan. 1, 2007, pp. 789-796.
Boffito Marta et al: "Pharmacokinetics and antiretroviral response to darunavir/ritonavir and etravirine combination in patients with high-level viral resistance", AIDS, London, GB, val. 21, No. 11, Jul. 1, 2007, pp. 1449-1455.
Busse K H S et al: "Darunavir: a second-generation protease inhibitor", Amerrican Journal of Health-System Pharmacy, American Society of Health-System Pharmacists, United States, val. 64, No. 15, Jan. 1, 2007, pp. 1593-1602.
Arun K. Ghosh et al: "Design of HIV Protease Inhibitors Targeting Protein Backbone: An Effective Strategy for Combating Drug Resistance", Accounts of Chemical Research, val. 41, No. 1, Jan. 1, 2008 pp. 78-86.

* cited by examiner

*Primary Examiner* — Shengjun Wang
(74) *Attorney, Agent, or Firm* — Perkins Coie LLP

(57) ABSTRACT

Compositions and methods of treating viral infections are provided. More particularly, compositions including a combination of protease inhibitors and cytochrome p450 enzyme inhibitors are provided. Methods of using the compositions for treatment of diseases or disorders caused by a virus such as HIV infections are also provided.

18 Claims, 23 Drawing Sheets

Figure 1

| COMPOUND | STRUCTURE | Molecular Formula | MW |
|---|---|---|---|
| 201 | 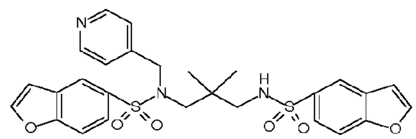 | C27H27N3O6S2 | 553.66 |
| 202 | 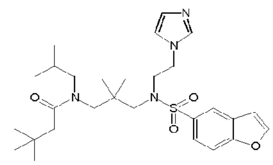 | C28H42N4O4S | 530.73 |
| 203 | 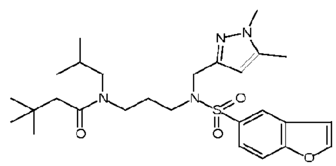 | C27H40N4O4S | 516.70 |
| 204 | 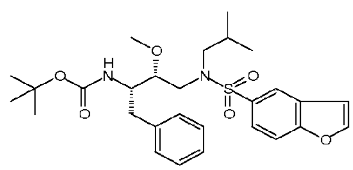 | C28H38N2O6S | 530.68 |
| 205 | 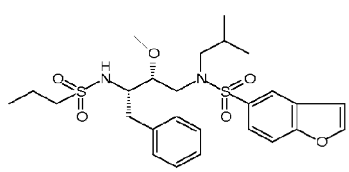 | C26H36N2O6S2 | 536.71 |
| 206 | 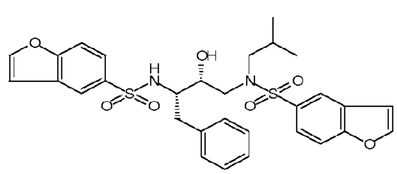 | C30H32N2O7S2 | 596.72 |
| 207 | 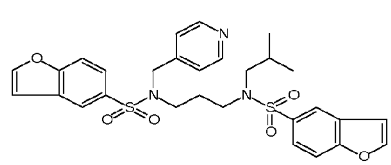 | C29H31N3O6S2 | 581.71 |
| 208 | 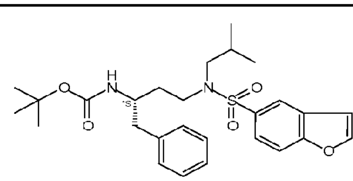 | C27H36N2O5S | 500.66 |

Figure 1 (continued)

| 209 | | C33H32N4O6S2 | 644.77 |
|---|---|---|---|
| 210 | | C29H39N3O3 | 477.65 |
| 211 | | C27H40N4O4S | 516.70 |
| 212 | | C30H34N2O6S | 550.67 |
| 213 | | C27H37N3O4S | 499.67 |
| 214 | | C26H33N3O3 | 435.57 |
| 215 | | C26H34N2O6S | 502.63 |
| 216 | | C27H37N3O4S | 499.67 |

| 217 |  | C27H37N3O4S | 499.67 |
|---|---|---|---|
| 218 |  | C29H41N3O4S | 527.73 |
| 219 |  | C30H38N2O8S | 586.70 |
| 220 |  | C26H37N3O4S2 | 519.73 |
| 221 |  | C29H31N3O4 | 485.58 |
| 222 |  | C26H35N3O5S | 501.65 |
| 223 |  | C28H39N3O5S | 529.70 |
| 224 |  | C31H28N4O6S2 | 616.71 |

| 225 |  | C31H39N3O4S | 549.73 |
|---|---|---|---|
| 226 |  | C28H31N3O6S3 | 601.76 |
| 227 |  | C26H33N3O4 | 451.57 |
| 228 |  | C27H36N2O6S | 516.66 |
| 229 |  | C30H34N2O6S | 550.67 |
| 230 |  | C29H40N2O5S | 528.71 |
| 231 |  | C27H36N2O6S | 516.66 |
| 232 |  | C29H30N6O6S2 | 622.72 |

| 233 |  | C28H39N3O4S | 513.70 |
|---|---|---|---|
| 234 |  | C26H38N4O4S | 502.68 |
| 235 |  | C39H32N4O6S2 | 716.83 |
| 236 |  | C26H38N4O4S | 502.68 |
| 237 |  | C28H32N4O5S | 536.65 |
| 238 |  | C29H38N4O4S | 538.71 |
| 239 |  | C29H25N3O6S2 | 575.66 |
| 240 |  | C30H31F3N2O5S | 588.64 |

| 241 |  | C28H32N4O6S2 | 584.71 |
|---|---|---|---|
| 242 |  | C25H37N5O4S | 503.67 |
| 243 |  | C24H32N2O6S2 | 508.66 |
| 244 |  | C27H36N2O6S | 516.66 |
| 245 |  | C24H24N4O6S2 | 528.61 |
| 246 |  | C26H37N3O4S2 | 519.73 |
| 247 |  | C28H39N3O5S | 529.70 |
| 248 |  | C26H37N3O4S2 | 519.73 |

| 249 |  | C26H35N3O4S | 485.65 |
|---|---|---|---|
| 250 |  | C27H34N4O4S3 | 574.78 |
| 251 |  | C29H31N3O4 | 485.58 |
| 252 |  | C30H43N3O5S | 557.75 |
| 253 |  | C25H38N2O4 | 430.59 |
| 254 |  | C28H38N2O6S | 530.68 |
| 255 |  | C27H36N2O5S | 500.66 |
| 256 |  | C26H35N3O5S | 501.65 |

Figure 1 (continued)

| 257 | | C31H28N4O6S2 | 616.71 |
|---|---|---|---|
| 258 | | C35H36N6O7S2 | 716.84 |
| 259 | | C28H41N3O4S2 | 547.78 |
| 260 | | C27H36N2O6S | 516.66 |
| 261 | | C25H38N2O4 | 430.59 |
| 262 | | C26H38N4O4S | 502.68 |
| 263 | | C26H36N4O3 | 452.60 |
| 264 | | C25H33N3O3S | 455.62 |

| 265 |  | C28H36N2O5 | 480.60 |
| --- | --- | --- | --- |
| 266 |  | C30H33N3O5 | 515.61 |
| 267 |  | C24H33N3O4S2 | 491.67 |
| 268 |  | C23H29N3O4S | 443.57 |
| 269 |  | C28H35N3O6S | 541.67 |
| 270 |  | C31H36N2O6S | 564.70 |
| 271 |  | C26H34N2O5S | 486.63 |
| 272 |  | C27H37N3O5S | 515.67 |

| 273 |  | C25H30N2O6S2 | 518.65 |
|---|---|---|---|
| 274 |  | C32H32N2O5 | 524.62 |
| 275 |  | C26H42N2O5S | 494.69 |
| 276 |  | C27H34N2O7S | 530.64 |
| 277 |  | C29H41N3O4S | 527.73 |
| 278 |  | C28H41N3O4S2 | 547.78 |
| 279 |  | C25H36N4O4S | 488.65 |
| 280 |  | C29H41N3O4S | 527.73 |

Figure 1 (continued)

| 281 | | C25H34N2O6S2 | 522.68 |
|---|---|---|---|
| 282 | | C24H38N2O5S | 466.64 |
| 283 | | C29H38N2O6S2 | 574.76 |
| 284 | | C27H36N2O5S | 500.66 |
| 285 | | C23H36N2O4S | 436.61 |
| 286 | | C29H40N6O4S | 568.74 |
| 287 | | C29H32N2O5S | 520.65 |
| 288 | | C28H37ClN2O6S | 565.13 |

Figure 1 (continued)

| 289 | | C25H23N3O6S2 | 525.60 |
|---|---|---|---|
| 290 | | C28H38N2O6S | 530.68 |
| 291 | | C22H27N3O5S | 445.54 |
| 292 | | C28H38N2O6S | 530.68 |
| 293 | | C29H40N2O6S | 544.71 |
| 294 | | C27H36N2O6S | 516.66 |
| 295 | | C29H44N4O4S | 544.76 |
| 296 | | C21H25N3O5S | 431.51 |

Figure 1 (continued)

| 297 | | C27H34N2O6S2 | 546.70 |
|---|---|---|---|
| 298 | | C28H37N3O4 | 479.62 |
| 299 | | C32H41N3O7S2 | 643.82 |
| 300 | | C28H38N2O6S | 530.68 |
| 301 | | C26H35N3O5S | 501.65 |
| 302 | | C23H26N2O6S2 | 490.60 |
| 303 | | C24H36N2O5S | 464.62 |
| 304 | | C22H27N3O5S | 445.54 |

| 305 |  | C25H23N3O6S2 | 525.60 |
| --- | --- | --- | --- |
| 306 |  | C27H40N4O4S | 516.70 |
| 307 |  | C21H32N2O4S | 408.56 |
| 308 |  | C23H30N2O6S2 | 494.63 |
| 309 |  | C27H35N3O3 | 449.59 |
| 310 |  | C27H36N2O5S | 500.66 |
| 311 |  | C23H29N3O4S | 443.57 |
| 312 |  | C31H28N4O6S2 | 616.71 |

| | | | |
|---|---|---|---|
| 313 |  | C29H38N2O7S | 558.69 |
| 314 |  | C25H38N2O7S | 510.65 |
| 315 |  | C23H29N3O5S | 459.56 |
| 316 |  | C25H38N2O4 | 430.59 |
| 317 |  | C22H29N3O4S2 | 463.62 |
| 318 |  | C22H29N3O4S2 | 463.62 |
| 319 |  | C25H33N3O4S | 471.62 |
| 320 |  | C27H44N2O4S | 492.72 |

| 321 |  | C23H28N2O5S | 444.55 |
|---|---|---|---|
| 322 |  | C27H36N2O5S | 500.66 |
| 323 |  | C28H38N2O5S | 514.68 |
| 324 |  | C27H30N4O6S2 | 570.69 |
| 325 |  | C28H41N3O4S2 | 547.78 |
| 326 |  | C22H28N4O4S | 444.55 |
| 327 |  | C30H33ClN2O6S | 585.12 |
| 328 |  | C23H28N2O5S | 444.55 |

Figure 1 (continued)

| | | | |
|---|---|---|---|
| 329 | | C24H38N2O5S | 466.64 |
| 330 | | C24H32N2O6S2 | 508.66 |
| 331 | | C29H28N4O6S4 | 656.82 |
| 332 | | C28H31N3O4S | 505.64 |
| 333 | | C37H38N2O6S | 638.78 |
| 334 | | C23H28N2O5S | 444.55 |
| 335 | | C22H34N2O6S | 454.59 |
| 336 | | C28H38N2O6S | 530.68 |

| 337 |  | C27H38N2O6S2 | 550.74 |
| 338 |  | C28H37N3O6S | 543.68 |
| 339 |  | C29H40N6O4S | 568.74 |
| 340 |  | C24H23N3O6S3 | 545.65 |
| 341 |  | C22H27N3O4S | 429.54 |
| 342 |  | C23H36N2O5S | 452.61 |
| 343 |  | C23H36N2O4S | 436.61 |
| 344 |  | C29H40N2O5S | 528.71 |

Figure 1 (continued)

| 345 | | C25H23N3O6S2 | 525.60 |
|---|---|---|---|
| 346 | | C26H35N3O5S | 501.65 |
| 347 | | C25H40N2O5S | 480.67 |
| 348 | | C34H42N2O6S | 606.78 |
| 349 | | C23H32N4O4S | 460.60 |
| 350 | | C21H30N2O4 | 374.48 |
| 351 | | C31H38N2O5S | 550.72 |
| 352 | | C27H36N2O6S | 516.66 |

| 353 |  | C22H26N2O5S | 430.52 |
|---|---|---|---|
| 354 |  | C24H30N2O5S | 458.58 |
| 355 |  | C30H34N2O5S | 534.67 |
| 356 |  | C21H32N2O4S | 408.56 |
| 357 |  | C27H42N2O5S | 506.71 |
| 358 |  | C26H42N2O5S | 494.69 |
| 359 |  | C25H25N3O6S2 | 527.62 |
| 360 |  | C27H42N2O5S | 506.71 |

| 361 |  | C25H39N3O4 | 445.60 |
| --- | --- | --- | --- |
| 362 |  | C33H40N2O5S | 576.76 |
| 363 |  | C28H38N2O5S | 514.68 |
| 364 |  | C23H26N2O6S2 | 490.60 |
| 365 |  | C23H34N2O5S | 450.60 |
| 366 |  | C23H27N3O4 | 409.49 |
| 367 |  | C26H42N2O5S | 494.69 |
| 368 |  | C22H34N2O5S | 438.59 |

HIV PROTEASE INHIBITOR AND CYTOCHROME P450 INHIBITOR COMBINATIONS

This application is the National Stage of International Application PCT/US2009/034926, filed Feb. 23, 2009, which claims the benefit of U.S. Provisional Application 61/030,531 filed Feb. 23, 2008, the contents of each of which are herein incorporated by reference in their entireties.

FIELD OF THE TECHNOLOGY

The technology relates to compositions and methods of treating viral infections. More particularly, the technology relates to compositions including a combination of protease inhibitors and cytochrome p450 enzyme inhibitors. The technology further relates to methods of using the compositions for treatment of diseases or disorders caused by a virus such as HIV infections.

BACKGROUND OF THE TECHNOLOGY

Infection by the retrovirus known as human immunodeficiency virus (HIV) continues to be a serious human health problem. Methods for treating HIV infections include administering agents which inhibit the activity of viral enzymes which are essential to the life cycle of the virus.

The genomes of retroviruses encode a protease that is responsible for the proteolytic processing of one or more polyprotein precursors such as the pol and gag gene products. Retroviral proteases most commonly process the gag precursor into core proteins, and also process the pol precursor into reverse transcriptase and retroviral protease.

The field of viral chemotherapeutics has developed in response to the need for agents effective against retroviruses, in particular HIV. Theoretically, there are many ways in which an agent can exhibit anti-retroviral activity. The HIV genome encodes several viral-specific enzymes, such as reverse transcriptase (RT), integrase, and protease (PR); viral-specific regulatory proteins, such as tat, rev, nef, and vif; and, numerous viral-specific structural proteins, and numerous viral-specific structural proteins, such as capsid, nucleocapsid, matrix, and envelope proteins. Many of these proteins are essential for viral replication. Accordingly, viral replication theoretically could be inhibited through inhibition of any one or all of the proteins involved in viral replication. In practice, however, only inhibitors of RT and PR are currently available for antiviral therapy.

Nucleoside analogues (NRTIs), such as 3'-azido-2',3'-dideoxythymidine (AZT), 2',3'-dideoxycytidine (ddC), and 2',3'-dideoxyinosine (ddI) are known to inhibit HIV RT. There also exist non-nucleoside inhibitors (NNRTIs) specific for HIV-1 RT, such as Nevirapine, and Efavirenz.

Retroviral PR inhibitors (PIs) have also been identified as a class of anti-retroviral agents. The retroviral PR processes polyprotein precursors into viral structural proteins and replicative enzymes. This processing is essential for the assembly and maturation of fully infectious virions. Accordingly, the design of PIs that selectively inhibit PR has been an important therapeutic goal in the treatment of HIV infections and AIDS. Strategies used in the design of HIV PIs include substrate-based, peptidomimetic, transition state-based, and structure-based drug design (Wlodawer & Erickson, *Ann. Rev. Biochem.*, 62, 543-585 (1992)).

Numerous classes of potent peptidic inhibitors of PR have been designed using the natural cleavage site of the precursor polyproteins as a starting point. These inhibitors typically are peptide substrate analogs in which the scissile P1-P1' amide bond has been replaced by a non-hydrolyzable isostere with tetrahedral geometry (Moore et al., *Perspect. Drug Dis. Design*, 1, 85 (1993); Tomasselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)).

The design of HIV-1 PIs based on the transition-state mimetic concept has led to the generation of a variety of peptide derivatives highly active against viral replication in vitro (Erickson et al., *Science*; 249, 527-533 (1990); Kramer et al., *Science*, 231, 1580-1584 (1986); McQuade et al., *Science*, 247, 454-456 (1990); Meek et al., *Nature* (London), 343, 90-92 (1990); Roberts et al., *Science*, 248, 358-361 (1990)). These active agents contain a non-hydrolyzable, dipeptide isostere such as hydroxyethylene (McQuade et al., supra; Meek et al., *Nature* (London), 343, 90-92 (1990); Vacca et al., *J. Med. Chem.*, 34, 1225-1228 (1991)) or hydroxyethylamine (Rich et al., *J. Med. Chem.*, 33, 1285-1288 (1990); Roberts et al., *Science*, 248, 358-361 (1990)) as an active moiety which mimics the putative transition state of the aspartic protease-catalyzed reaction.

Two-fold (C2) symmetric inhibitors of HIV protease represent another class of potent HIV PIs which were created by Erickson et al. on the basis of the three-dimensional symmetry of the enzyme active site (Erickson et al., supra).

Typically, the usefulness of currently available HIV PIs in the treatment of AIDS has been limited by relatively short plasma half-life, poor oral bioavailability, and the technical difficulty of scale-up synthesis (Meek et al. (1992), supra). Although these inhibitors are effective in preventing the retroviral PR from functioning, the inhibitors suffer from some distinct disadvantages. Generally, peptidomimetics make poor drugs due to their potential adverse pharmacological properties, i.e., poor oral absorption, poor stability, and rapid metabolism (Plattner et al., Drug Discovery Technologies, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired. Those inhibitors that do bind are generally poorly water-soluble, causing distinct problems for formulation and drug delivery.

Some drugs and, in particular, some HIV protease inhibitors are metabolized by cytochrome P450 monooxygenase, leading to unfavorable pharmacokinetics and the need for more frequent and higher doses than are most desirable. Therefore, administration of such drugs with an agent that inhibits metabolism by cytochrome P450 monooxygenase can improve the pharmacokinetics (i.e., increase half-life, increase the time to peak plasma concentration, increase blood levels) of the drug.

However, present methods of inhibiting cytochrome P450 enzymes are not wholly satisfactory because of toxicity issues, high cost, and other such factors. It is apparent, therefore, that new and improved agents and methods of inhibiting cytochrome P450 enzymes are greatly to be desired. In particular, compositions and methods where the cytochrome p450 enzyme inhibitor can be co-administered with another biologically active compound that is metabolized by cytochrome P450 enzymes are highly desirable.

SUMMARY OF THE TECHNOLOGY

The technology provides compositions and methods of treating viral infections. More particularly, the technology provides compositions including a combination of protease inhibitors and cytochrome p450 enzyme inhibitors. The technology further provides methods of using the compositions for treatment of diseases or disorders caused by a virus such as HIV infections.

An advantage of the technology is that it provides improved combinations of protease inhibitors and inhibitors of cytochrome P450 enzymes. Another advantage is that it provides a method of modifying or controlling the pharmacokinetic properties of protease inhibitors. A further advantage is that it helps control the rate of metabolism or degradation of protease inhibitors, thereby enhancing the bioavailability of protease inhibitors. This enhances the efficacy of protease inhibitors and can permit protease inhibitors to be administered at a lower concentration or dosage, which reduces, for example, their toxicity. Another advantage is that these properties can lower the overall cost associated with the treatment of disorders including viral infections.

More particularly, in one aspect, the technology provides a composition including a compound of formula I and a compound of formula II in an amount effective to treat a disease or disorder:

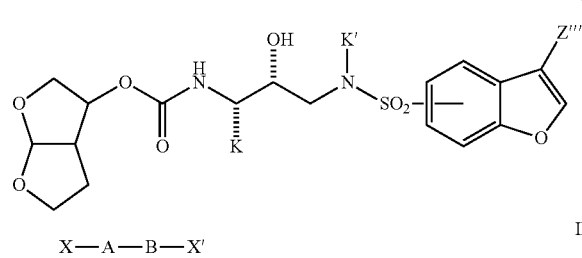

where:

K is aralkyl optionally substituted with one or more groups selected from alkyl, halo, nitro, cyano, $CF_3$, C3-C7 cycloalkyl, C5-C7 cycloalkenyl, R6, OR2, SR2, NHR2, OR3, SR3, NHR3, OR6, SR6, or NHR6;

K' is alkyl;

Z''' is C1-C6 alkyl substituted with $N(R)CO_nR$;

X is a lipophilic group containing from 1 to 12 carbon atoms optionally containing from 1 to 3 heteroatoms independently selected from the group consisting of O, S, and N, A is —OCON(R2)-, —S(O)$_n$N(R2)-, —CON(R2)-, —COCO(NR2)-, —N(R2)CON(R2)-, —N(R2)S(O)$_n$N (R2)-, N(R2)CO or —N(R2)COO—;

B is —(CG$_1$G$_2$)$_m$-, where m is 2-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, $CF_3$, OR, $C_3$-$C_7$ cycloalkyl, $C_5$-$C_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

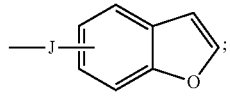

where J is selected from:
—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, where D optionally is substituted by alkyl, halo, nitro, cyano, O-alkyl, or S-alkyl;

where R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, =N—OR, =N—$N(R)_2$, =NR, =NNRC(O)$N(R)_2$, =NNRCO$_n$R, =NNRS(O)$_n$N(R)_2$, and =NNRS(O)$_n$(R);

or each R2 is independently selected from the group consisting of $C_1$-$C_6$ alkyl; substituted by aryl or heteroaryl; which groups optionally are substituted with one or more substituents selected from the group consisting of halo, OR, ROH, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N (R)_2$, $N(R)N(R)CO_nR$, $NRPO_nN(R)_2$, $NRPO_nOR$;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, $NO_2$, CN, $CO_nR2$, $C(O)N(R2)_2$, $C(O)N(R2)N(R2)_2$, C(S)R2, C(S)$N(R2)_2$, S(O)$_n$N(R2)_2$, SR2, $SO_nR2$, $N(R2)_2$, $N(R2)CO_nR2$, $NR2S(O)_nR2$, $NR2C[=N(R2)]N(R2)_2$, $N(R2)N(R2)CO_nR2$, oxo, =N—OR2, =N—$N(R2)_2$, =NR2, =NNRC(O)$N(R2)_2$, =NNR2C(O)$_n$R2, =NNR2S(O)$_n$N(R2)_2$, and =NNR2S(O)$_n$(R2);

R6 is aryl or heteroaryl, where the aryl or heteroaryl optionally are substituted with one or more groups selected from the group consisting of aryl, heteroaryl, R2, R3, halo, OR2, R2OH, R2-halo, $NO_2$, CN, $CO_nR2$, $C(O)N(R2)_2$, $C(O)N(R2)N(R2)_2$, C(S)R2, $C(S)N(R2)_2$, $S(O)_nN(R2)_2$, SR2, $SO_nR2$, $N(R)_2$, $N(R2)CO_nR2$, $NR2S(O)_nR2$, $NR2C[=N (R2)]N(R2)_2$, $N(R2)N(R2)CO_nR2$, OC(O)R2, OC(S)R2, OC(O)$N(R2)_2$, and OC(S)$N(R2)_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, C(S)N$(R)_2$, $SO_nN(R)_2$, SR, $SO_nR$, $N(R)_2$, $N(R)CO_nR$, $NRS(O)_nR$, NRC[=N(R)]N$(R)_2$, N(R)N(R)$CO_nR$, $NRPO_nN(R)_2$, $NRPO_nOR$, oxo, =N—OR, =N—N$(R)_2$, =NR, =NNRC(O)N$(R)_2$, =NNR$CO_nR$, =NNRS(O)$_n$N$(R)_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and where q=0-1, provided that: when X is a 5-7 membered non-aromatic monocyclic heterocycle, optionally fused or bridged with one or more 3-7 membered non-aromatic monocyclic heterocycle to form a polycyclic system, where any of the heterocyclic ring systems contains one or more heteroatoms selected from O, N, S, and P, and when B is where U is selected from optionally substituted alkyl, optionally substituted alkenyl, optionally substituted alkynyl, optionally substituted aryl, optionally substituted cycloalkyl, or optionally substituted aralkyl, then J cannot be —N(D)-SO$_n$— or —N(D)-CO$_n$—.

In another aspect, the technology provides a method of treating a disease associated with a viral infection, including administering to a subject suffering from the disease an effective amount of the above composition.

Each of the aspects described above can include one or more of the following embodiments.

X is selected from the group consisting of alkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl; where X optionally is substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, C(S)N$(R)_2$, $SO_nN(R)_2$, SR, $SO_nR$, $N(R)_2$, $N(R)CO_nR$, $NRS(O)_nR$, NRC[=N(R)]N$(R)_2$, N(R)N(R)$CO_nR$, $NRPO_nN(R)_2$, $NRPO_nOR$, oxo, =N—OR, =N—N$(R)_2$, =NR, =NNRC(O)N$(R)_2$, =NNR$CO_nR$, =NNRS(O)$_n$N$(R)_2$, and =NNRS(O)$_n$(R).

X is selected from the group consisting of alkyl, cycloalkyl, aryl, aralkyl, heteroaryl, and heteroaralkyl.

X optionally is substituted with one or more substituents selected from the group consisting of halo, OR, ROH, R-halo, CN, $CO_nR$, $CON(R)_2$, $SO_nN(R)_2$, SR, $SO_nR$, $N(R)_2$, N(R)$CO_nR$, $NRS(O)_nR$, oxo, and =N—OR.

X optionally is substituted with one or more substituents selected from the group consisting of halo, OR, $CO_nR$, $CON(R)_2$, $SO_nN(R)_2$, $SO_nR$, $N(R)_2$, N(R)$CO_nR$, and oxo.

$G_1$ and $G_2$ are the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl.

$G_1$ and $G_2$ do not form a ring.

At least one $G_1$ and at least one $O_2$ form a ring.

$G_1$ and $G_2$ are different.

Neither $G_1$ nor $G_2$ is OH.

G1 and G2 are selected from the group consisting of H, O-alkyl, alkyl, optionally substituted aryl and optionally substituted aralkyl.

J is

J is

J is

—N(D)-(R8)$_q$-.

J is

—SO$_n$—N(D)-(R8)$_q$-.

J is

—CO$_n$—N(D)-(R8)$_q$-.

D is selected from the group consisting of hydrogen, alkyl, cycloalkyl, cycloalkylalkyl, aryl, heteroaryl, heteroaralkyl and aralkyl, where D optionally is substituted by alkyl, halo, nitro, cyano, O-alkyl, or S-alkyl.

D optionally is substituted by alkyl, halo, or O-alkyl.

D is selected from the group consisting of hydrogen, alkyl, heteroaralkyl and aralkyl, where D optionally is substituted by alkyl, halo, nitro, cyano, O-alkyl, and S-alkyl.

K is benzyl, and K' is isobutyl.

The compound of formula I is

The compound of formula II is

The compound of formula I is

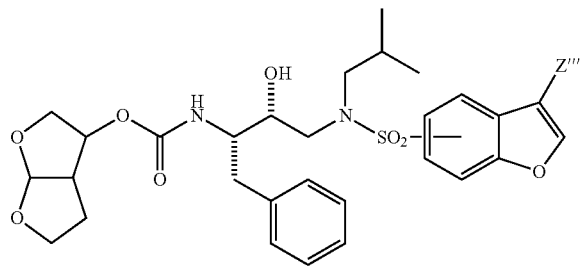

and the compound of formula II is

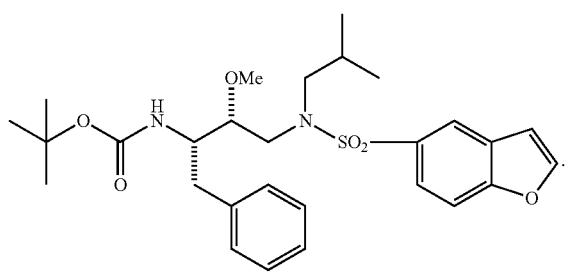

Z''' is —CH$_2$—N(R)CO$_n$R.
Z''' is —CH$_2$—NHCO$_n$R.
Z''' is —CH$_2$—NHCO$_2$Et.
The disease is an HIV infection.

The details of one or more examples are set forth in the accompanying reaction schemes and description. Further features, aspects, and advantages of the technology will become apparent from the description, the schemes, and the claims.

DETAILED DESCRIPTION

Figure 1:
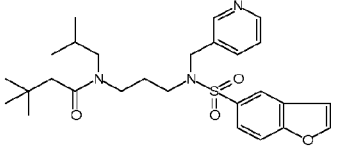
FIG. 1 shows examples of cytochrome P450 inhibitors of the technology. These examples are merely illustrative and not limiting of the present technology.
Figure 1:
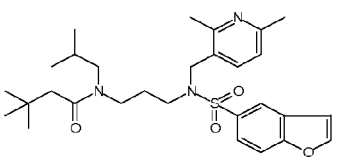
Figure 1:
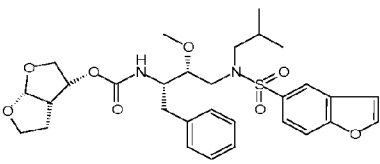
Figure 1:
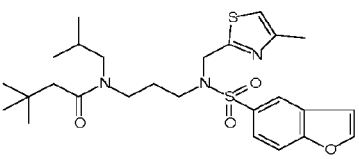
Figure 1:
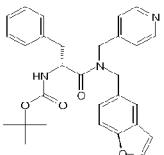
Figure 1:
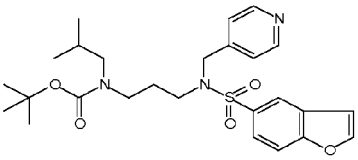
Figure 1:
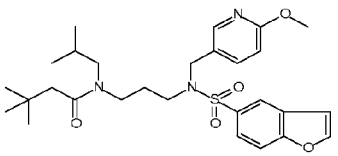
Figure 1:
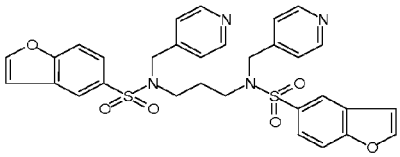
Figure 1:
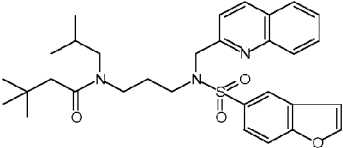
Figure 1:
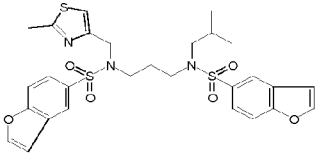
Figure 1:
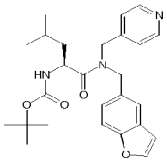
Figure 1:
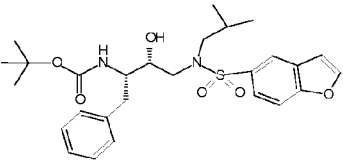
Figure 1:
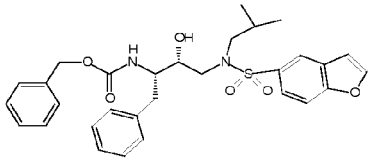
Figure 1:
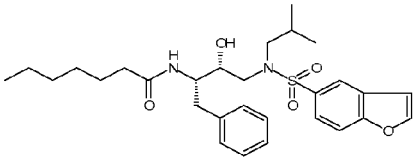
Figure 1:
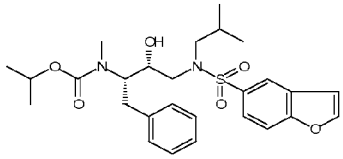
Figure 1:
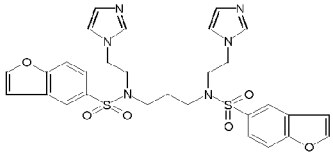
Figure 1:
Figure 1:
Figure 1:
Figure 1:
Figure 1:
Figure 1:
Figure 1:
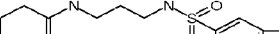
Figure 1:
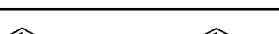
Figure 1:
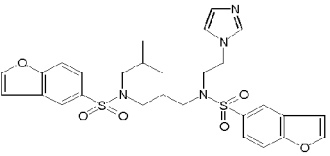
Figure 1:
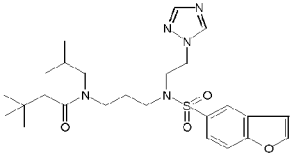
Figure 1:
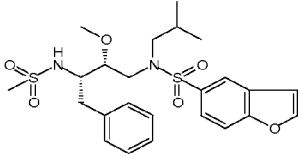
Figure 1:
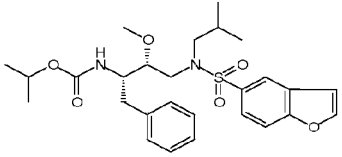
Figure 1:
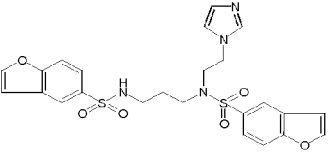
Figure 1:
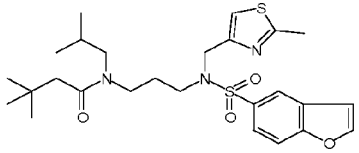
Figure 1:
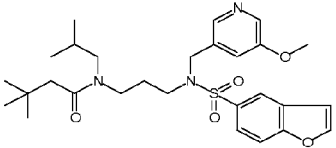
Figure 1:
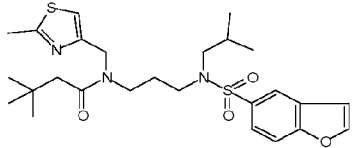
Figure 1:
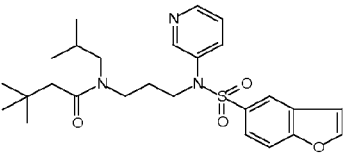
Figure 1:
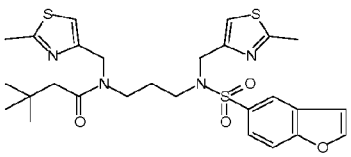
Figure 1:
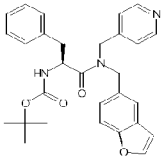
Figure 1:
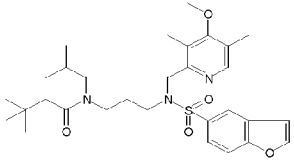
Figure 1:
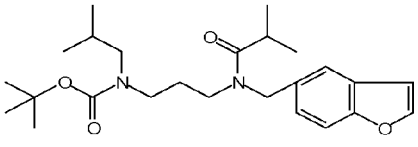
Figure 1:
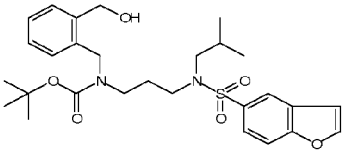
Figure 1:
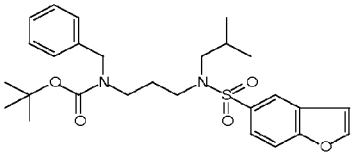
Figure 1:
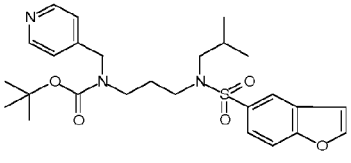
Figure 1:
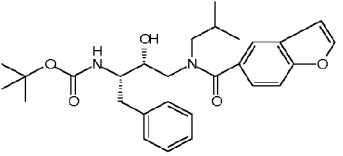
Figure 1:
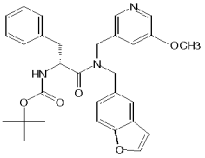
Figure 1:
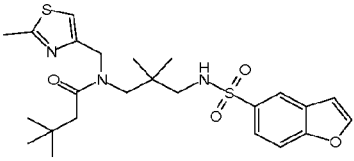
Figure 1:
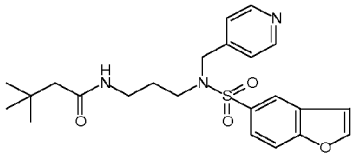
Figure 1:
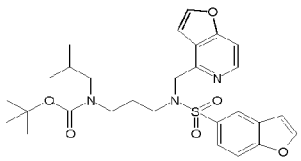
Figure 1:
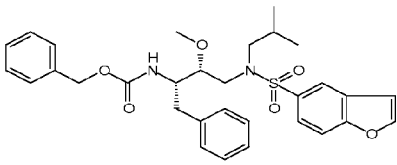
Figure 1:
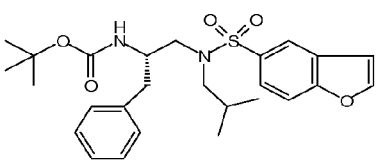
Figure 1:
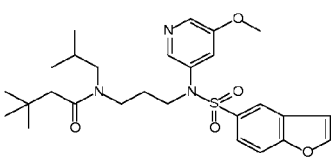
Figure 1:
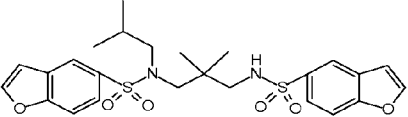
Figure 1:
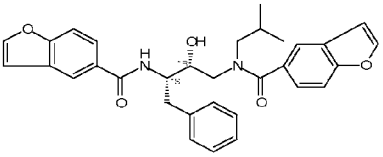
Figure 1:
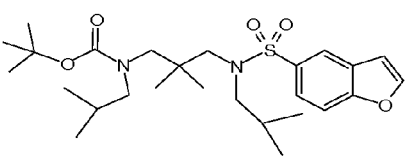
Figure 1:
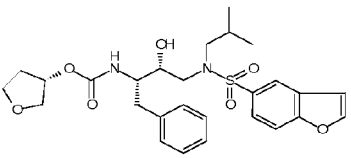
Figure 1:
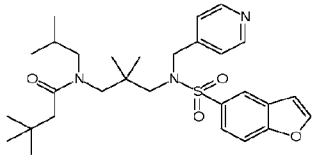
Figure 1:
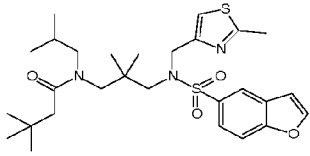
Figure 1:
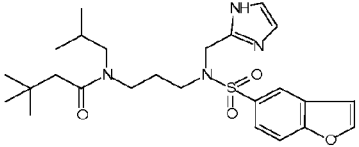
Figure 1:
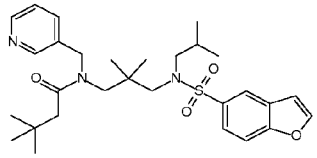
Figure 1:
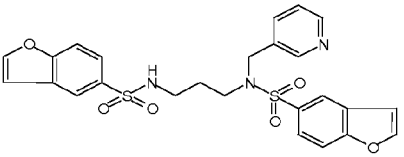
Figure 1:
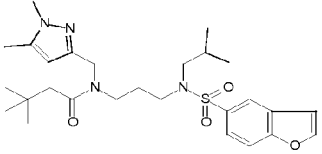
Figure 1:
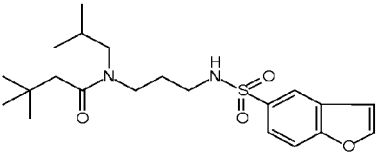
Figure 1:
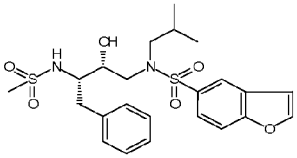
Figure 1:
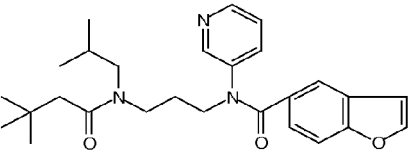
Figure 1:
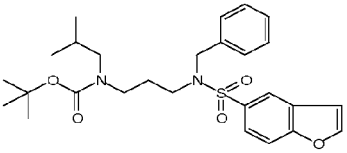
Figure 1:
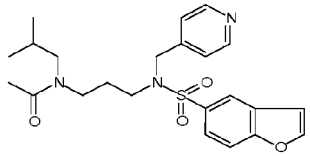
Figure 1:
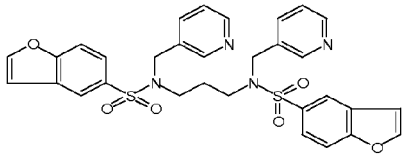
Figure 1:
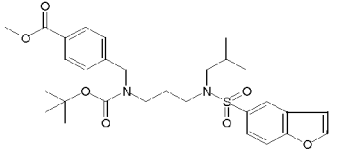
Figure 1:
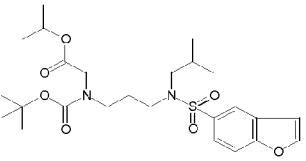
Figure 1:
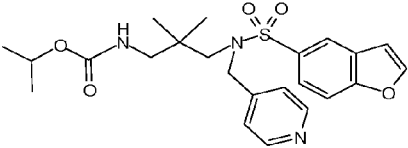
Figure 1:
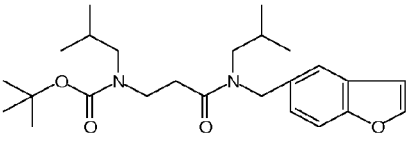
Figure 1:
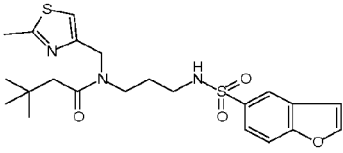
Figure 1:
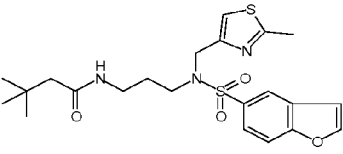
Figure 1:
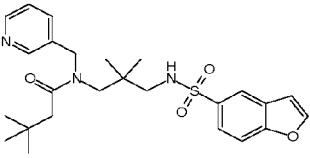
Figure 1:
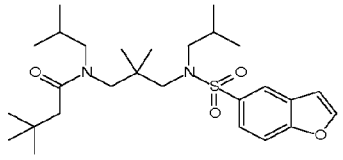
Figure 1:
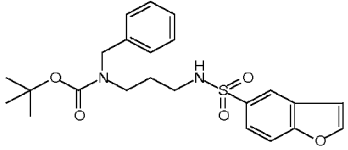
Figure 1:
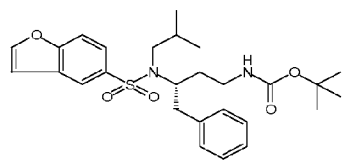
Figure 1:
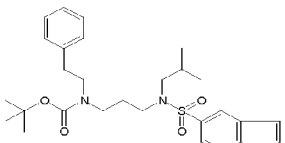
Figure 1:
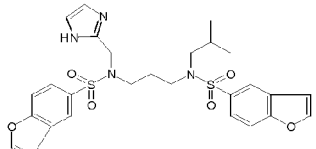
Figure 1:
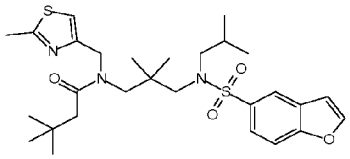
Figure 1:
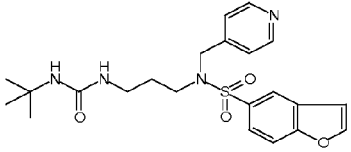
Figure 1:
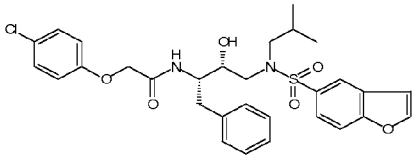
Figure 1:
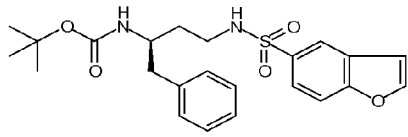
Figure 1:
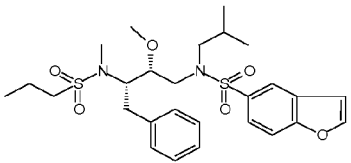
Figure 1:
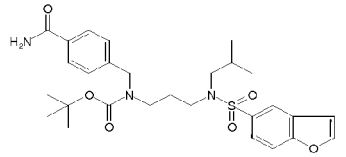
Figure 1:
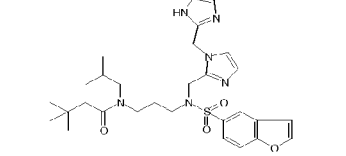
Figure 1:
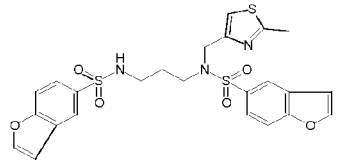
Figure 1:
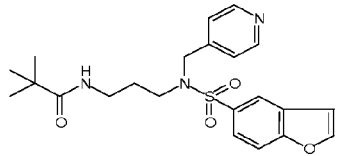
Figure 1:
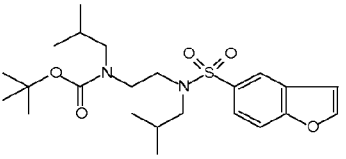
Figure 1:
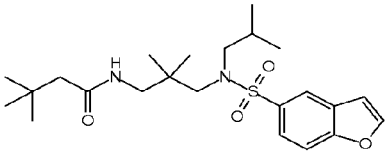
Figure 1:
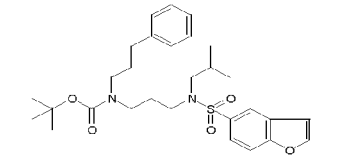
Figure 1:
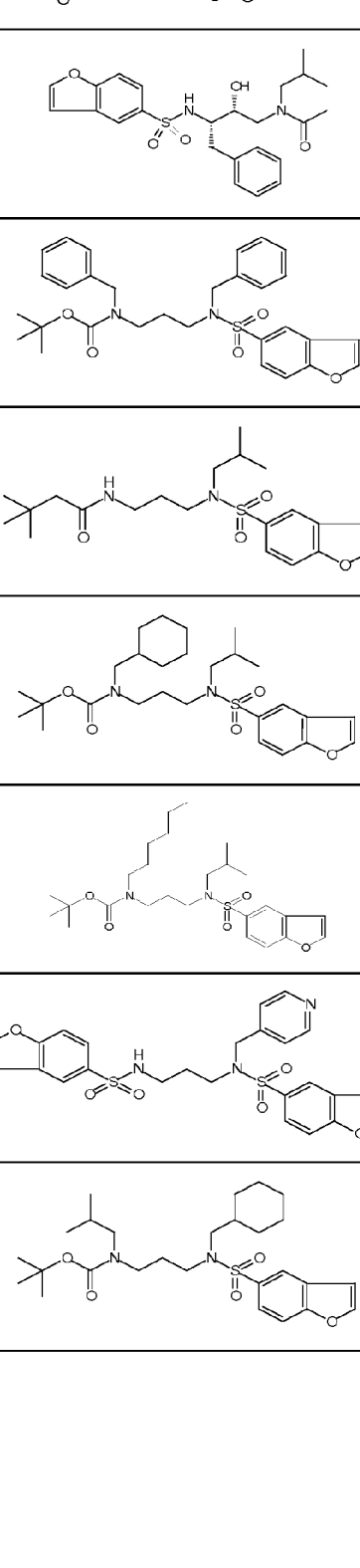
Figure 1:
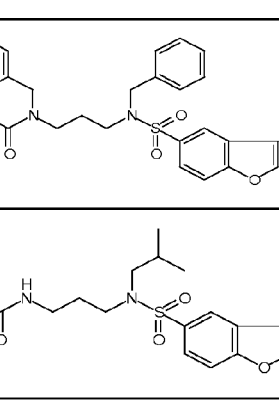
Figure 1:
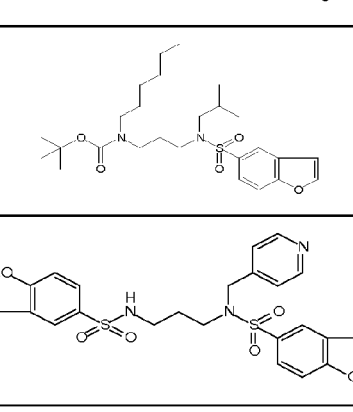
Figure 1:
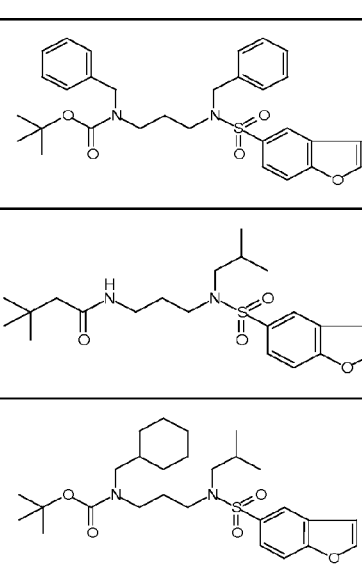
Figure 1:
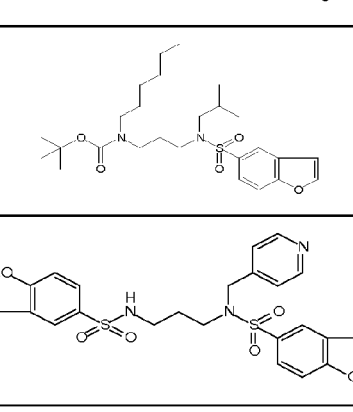
Figure 1:
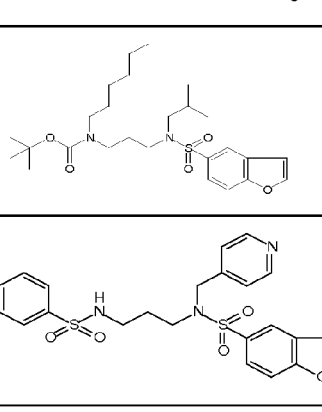
Figure 1:
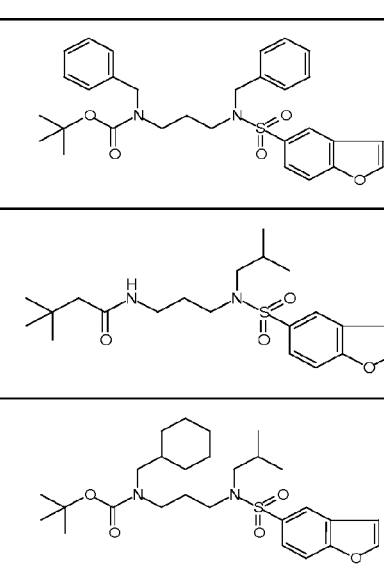
Figure 1:
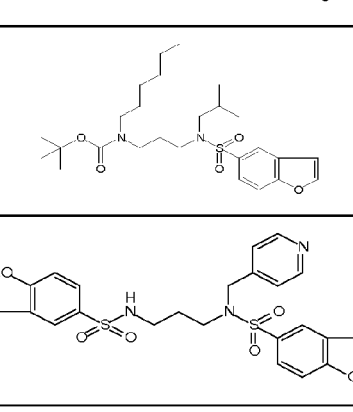
Figure 1:
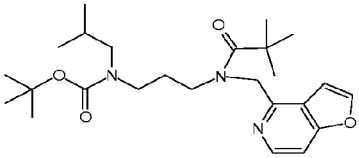
Figure 1:
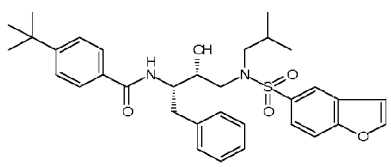
Figure 1:
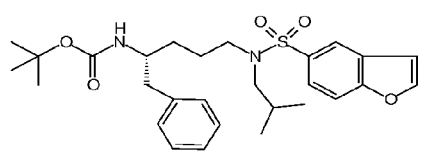
Figure 1:
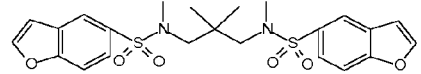
Figure 1:
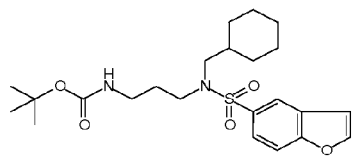
Figure 1:
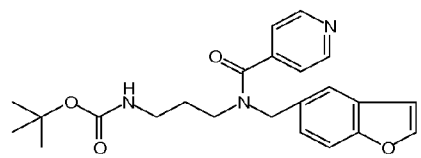
Figure 1:
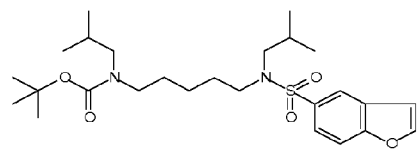
Figure 1:
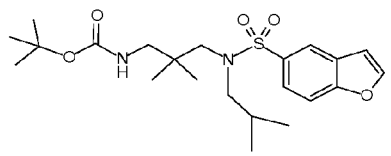
Figure 2:
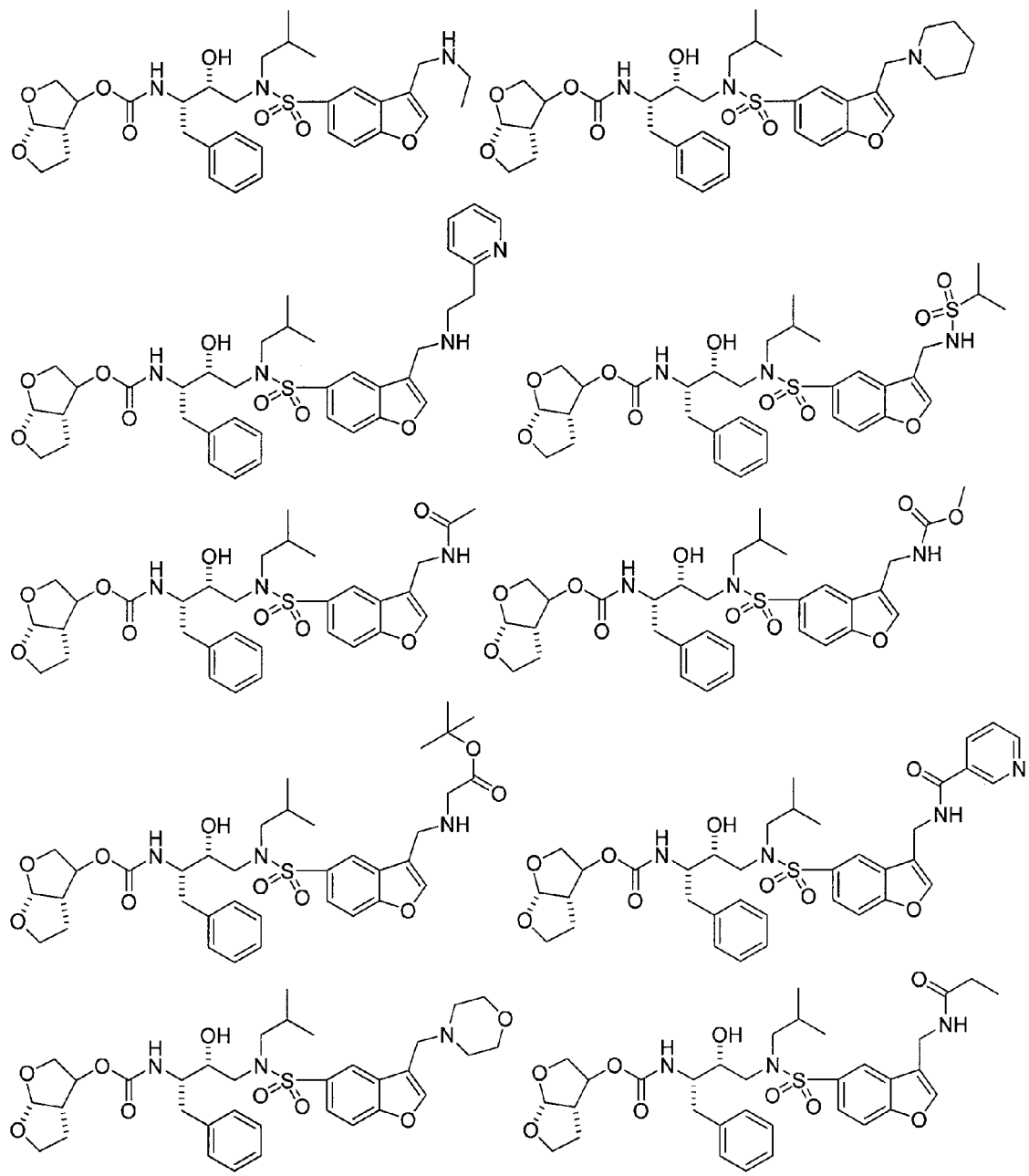
FIG. 2 shows examples of benzofuran containing HIV protease inhibitors.
Figure 2:
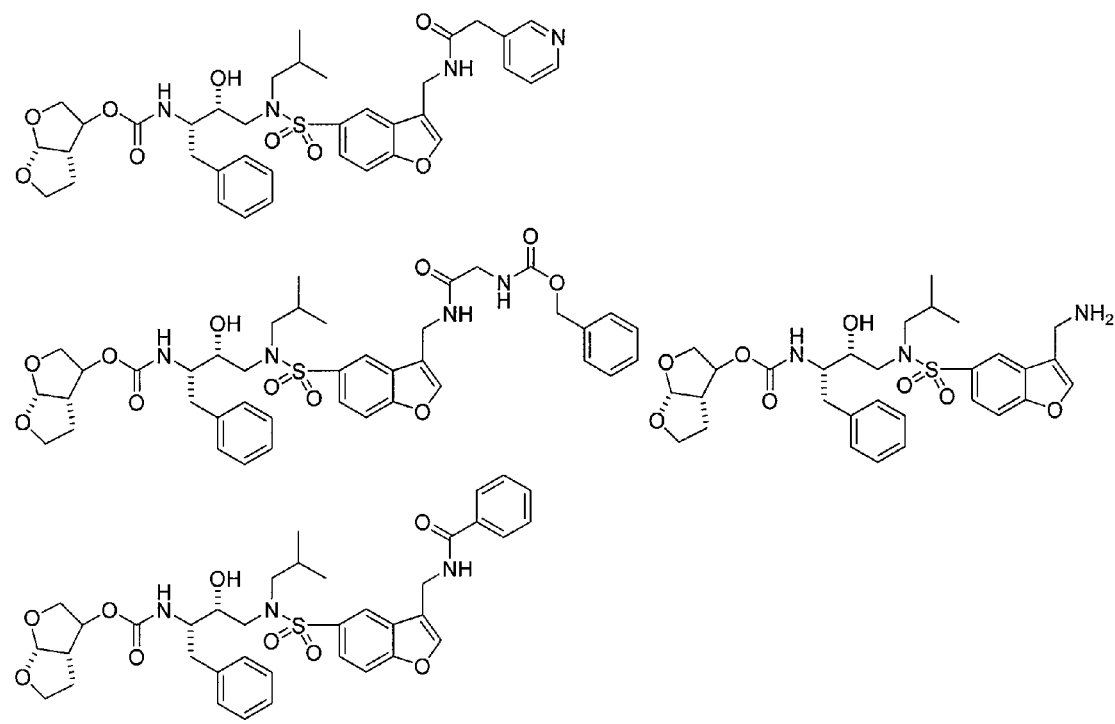

The technology provides compositions and methods of treating viral infections. More particularly, the technology provides compositions including a combination of protease inhibitors and cytochrome p450 enzyme inhibitors. The technology further provides methods of using the compositions for treatment of diseases or disorders caused by a virus such as HIV infections.

The technology provides methods of inhibiting cytochrome P450 (CYP) enzymes. The technology provides methods for enhancing the therapeutic effect of protease inhibitors in which the efficacy is compromised due to degradation mediated by cytochrome P450. The methods include administering compounds or pharmaceutical compositions containing the compounds in any therapeutic regimen where one or more protease inhibitors are metabolized by a CYP. The compounds or pharmaceutical compositions can be administered when the primary drug either becomes inactive or is converted to a toxic metabolite due to metabolism by a CYP. The compounds or compositions can inhibit or reduce the rate of degradation of protease inhibitors that are effective against a variety of viral infections and that are degraded by one or more cytochrome P450 enzymes. Upon co-administration, the compounds and compositions can, for example, maintain intracellular concentrations of the protease inhibitors at a therapeutic level for a sustained period of time. The methods are useful, for example, in treating a variety of infections such as HIV or HCV.

More particularly, in one aspect, the technology provides a composition including a compound of formula I and a compound of formula II in an amount effective to treat a disease or disorder:

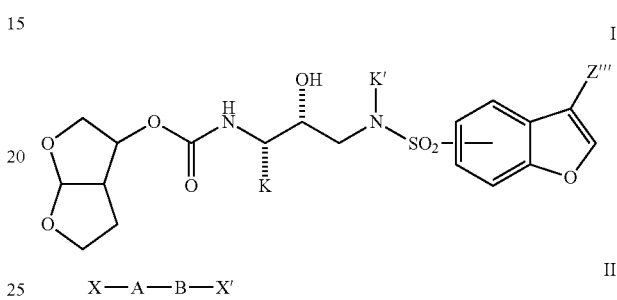

X—A—B—X' where:
K is aralkyl optionally substituted with one or more groups selected from alkyl, halo, nitro, cyano, CF$_3$, C$_3$-C$_7$ cycloalkyl, C$_5$-C$_7$ cycloalkenyl, R6, OR2, SR2, NHR2, OR3, SR3, NHR3, OR6, SR6, or NHR6;

K' is alkyl;

Z''' is C1-C6 alkyl substituted with N(R)CO$_n$R;

X is a lipophilic group containing from 1 to 12 carbon atoms optionally containing from 1 to 3 heteroatoms independently selected from the group consisting of O, S, and N, A is —OCON(R2)-, —S(O)$_n$N(R2)-, —CON(R2)-, —COCO(NR2)-, —N(R2)CON(R2)-, —N(R2)S(O)$_n$N(R2)-, N(R2)CO or —N(R2)COO—;

B is —(CG$_1$G$_2$)$_m$-, where m is 2-6 and where G$_1$ and G$_2$ are the same or different and where each G$_1$ and G$_2$ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, optionally substituted heteroaralkyl, and optionally substituted heterocycloalkyl where each optional substitution independently is selected from the group consisting of alkyl, halo, cyano, CF$_3$, OR, C$_3$-C$_7$ cycloalkyl, C$_5$-C$_7$ cycloalkenyl, R6, OR2, SR2, N(R2)$_2$, OR3, SR3, NR2R3, OR6, SR6, and NR2R6, and where G$_1$ and G$_2$, together with the atoms to which they are attached, optionally may form a 3-7-membered carbocyclic or heterocyclic ring containing up to three heteroatoms selected from the group consisting of N, S and O, and where the ring optionally may be substituted with up to 3 R7 moieties, X' is

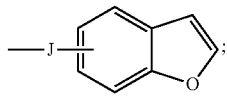

where J is selected from:
—N(D)-SO$_n$—, —N(D)-CO$_n$—, —N(D)-(R8)$_q$-, —N(CO-D)-(R8)$_q$-, —N(SO$_n$-D)-(R8)$_q$-, —SO$_n$—N(D)-(R8)$_q$-, or —CO$_n$—N(D)-(R8)$_q$-, where D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, where D optionally is substituted by alkyl, halo, nitro, cyano, O-alkyl, or S-alkyl;

where R is 1-1, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR, oxo, ═N—OR, ═N—N(R)$_2$, ═NR, ═NNRC(O)N(R)$_2$, ═NNRCO$_n$R, ═NNRS(O)$_n$N(R)$_2$, and ═NNRS(O)$_n$(R);

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[═N(R2)]N(R2)$_2$, N(R2)N(R2)CO$_n$R2, oxo, ═N—OR2, ═N—N(R2)$_2$, ═NR2, ═NNRC(O)N(R2)$_2$, ═NNR2C(O)$_n$R2, ═NNR2S(O)$_n$N(R2)$_2$, and ═NNR2S(O)$_n$(R2);

R6 is aryl or heteroaryl, where the aryl or heteroaryl optionally are substituted with one or more groups selected from the group consisting of aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[═N(R2)]N(R2)$_2$, N(R2)N(R2)CO$_n$R2, OC(O)R2, OC(S)R2, OC(O)N(R2)$_2$, and OC(S)N(R2)$_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR, oxo, ═N—OR, ═N—N(R)$_2$, ═NR, ═NNRC(O)N(R)$_2$, ═NNRCO$_n$R, ═NNRS(O)$_n$N(R)$_2$, and ═NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

where n=1-2, and
where q=0-1, provided that: when X is a 5-7 membered non-aromatic monocyclic heterocycle, optionally fused or bridged with one or more 3-7 membered non-aromatic monocyclic heterocycle to form a polycyclic system, where any of the heterocyclic ring systems contains one or more heteroatoms selected from O, N, S, and P, and when
B is

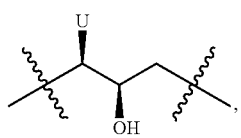

where U is selected from optionally substituted alkyl, optionally substituted alkenyl, optionally substituted alkynyl, optionally substituted aryl, optionally substituted cycloalkyl, or optionally substituted aralkyl, then J cannot be —N(D)-SO$_n$— or —N(D)-CO$_n$—.

In another aspect, the technology provides a method of treating a disease associated with a viral infection, including administering to a subject suffering from the disease an effective amount of the above composition.

Each of the aspects described above can include one or more of the following embodiments.

X is selected from the group consisting of alkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl; where X optionally is substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[═N(R)]N(R)$_2$, N(R)N(R)CO$_n$R, NRPO$_n$N(R)$_2$, NRPO$_n$OR, oxo, ═N—OR, ═N—N(R)$_2$, ═NR, ═NNRC(O)N(R)$_2$, ═NNRCO$_n$R, ═NNRS(O)$_n$N(R)$_2$, and ═NNRS(O)$_n$(R).

X is selected from the group consisting of alkyl, cycloalkyl, aryl, aralkyl, heteroaryl, and heteroaralkyl.

X optionally is substituted with one or more substituents selected from the group consisting of halo, OR, ROH, R-halo, CN, CO$_n$R, CON(R)$_2$, SO$_n$N(R)$_2$, SR, SO$_n$R, N(R)$_2$, N(R)CO$_n$R, NRS(O)$_n$R, oxo, and ═N—OR.

X optionally is substituted with one or more substituents selected from the group consisting of halo, OR, CO$_n$R, CON(R)$_2$, SO$_n$N(R)$_2$, SO$_n$R, N(R)$_2$, N(R)CO$_n$R, and oxo.

$G_1$ and $G_2$ are the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl.

$G_1$ and $G_2$ do not form a ring.
At least one $G_1$ and at least one $G_2$ form a ring.
$G_1$ and $G_2$ are different.
Neither $G_1$ nor $G_2$ is OH.
G1 and G2 are selected from the group consisting of H, O-alkyl, alkyl, optionally substituted aryl and optionally substituted aralkyl.

J is

J is

J is
—N(D)-(R8)$_q$-.
J is
—SO$_n$—N(D)-(R8)$_q$-.
J is
—CO$_n$—N(D)-(R8)$_q$-.

D is selected from the group consisting of hydrogen, alkyl, cycloalkyl, cycloalkylalkyl, aryl, heteroaryl, heteroaralkyl and aralkyl, where D optionally is substituted by alkyl, halo, nitro, cyano, O-alkyl, or S-alkyl.

D optionally is substituted by alkyl, halo, or O-alkyl.

D is selected from the group consisting of hydrogen, alkyl, heteroaralkyl and aralkyl, where D optionally is substituted by alkyl, halo, nitro, cyano, O-alkyl, and S-alkyl.

K is benzyl, and K' is isobutyl.

The compound of formula I is

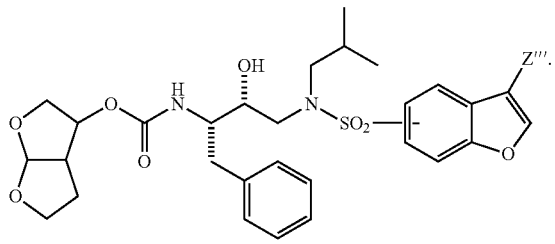

The compound of formula II is

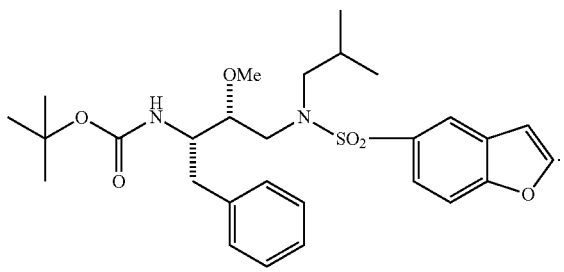 [SMILES: CO[C@H](CN(CC(C)C)S(=O)(=O)c1ccc2occc2c1)[C@H](Cc1ccccc1)NC(=O)OC(C)(C)C]

The compound of formula I is

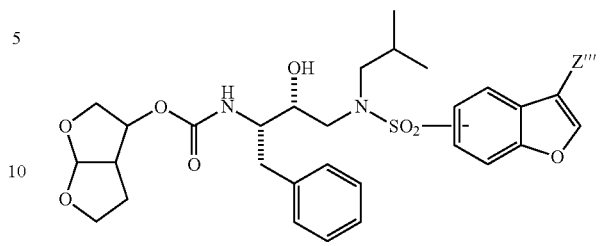

and the compound of formula II is

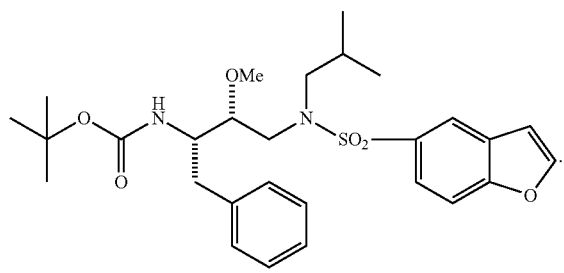 [SMILES: CO[C@H](CN(CC(C)C)S(=O)(=O)c1ccc2occc2c1)[C@H](Cc1ccccc1)NC(=O)OC(C)(C)C]

Z''' is —CH$_2$—N(R)CO$_n$R.

Z''' is —CH$_2$—NHCO$_n$R.

Z' is —CH$_2$—NHCO$_2$Et.

The disease is an HIV infection.

This technology also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products can be obtained by such quaternization.

The table below shows examples of various X, A, B and J moieties, although it will be recognized that these examples are merely illustrative and not limiting of the present technology.

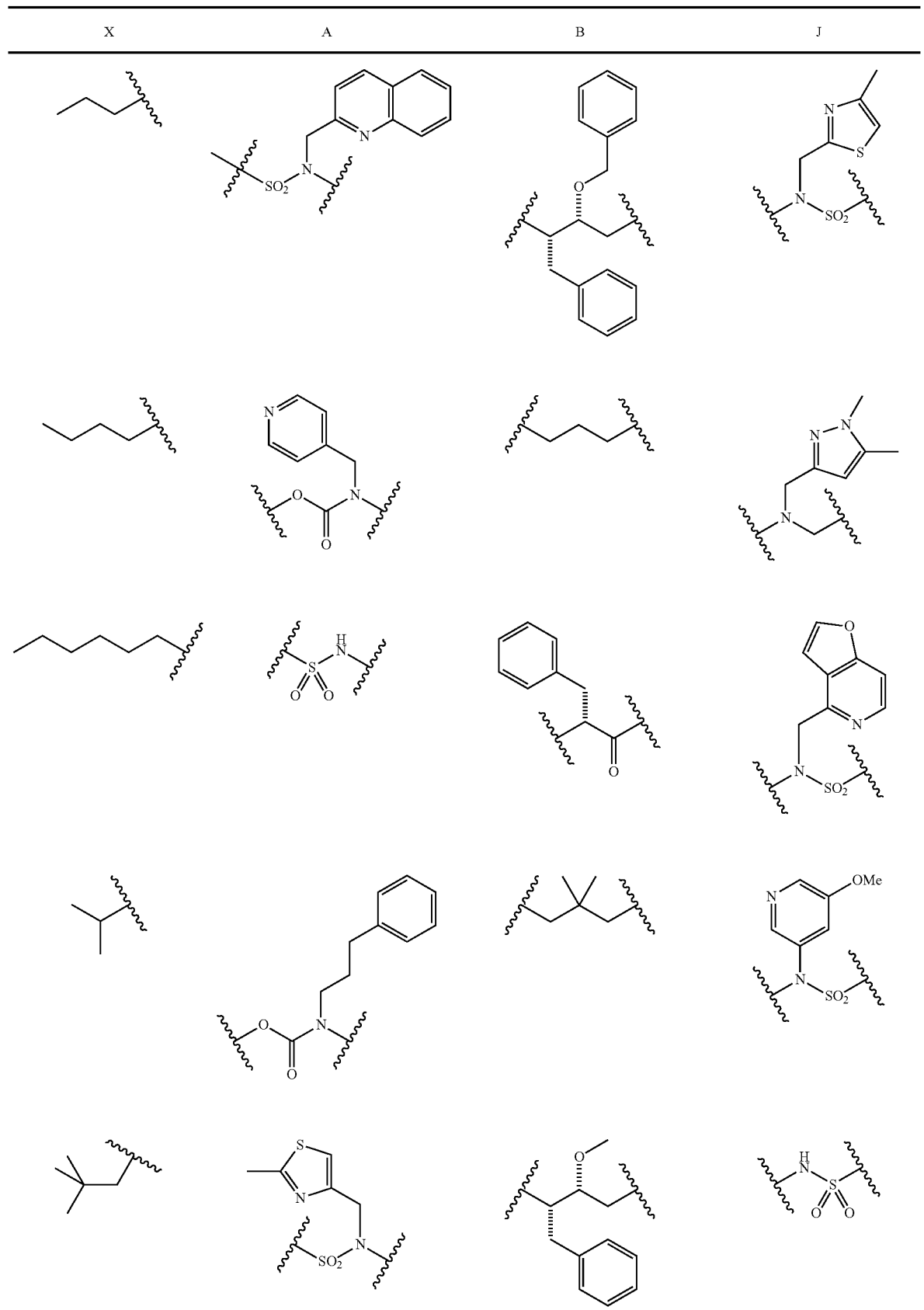

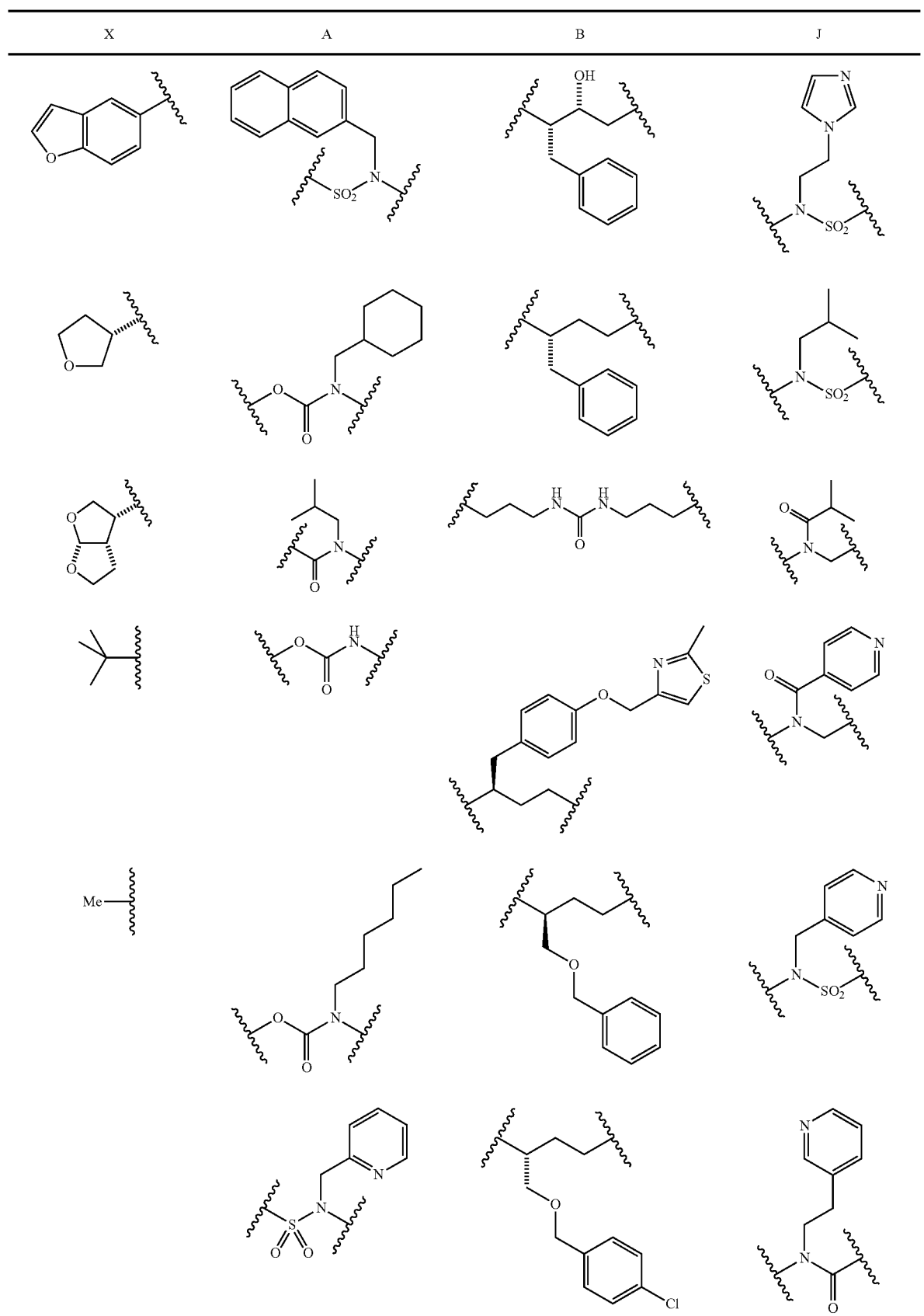

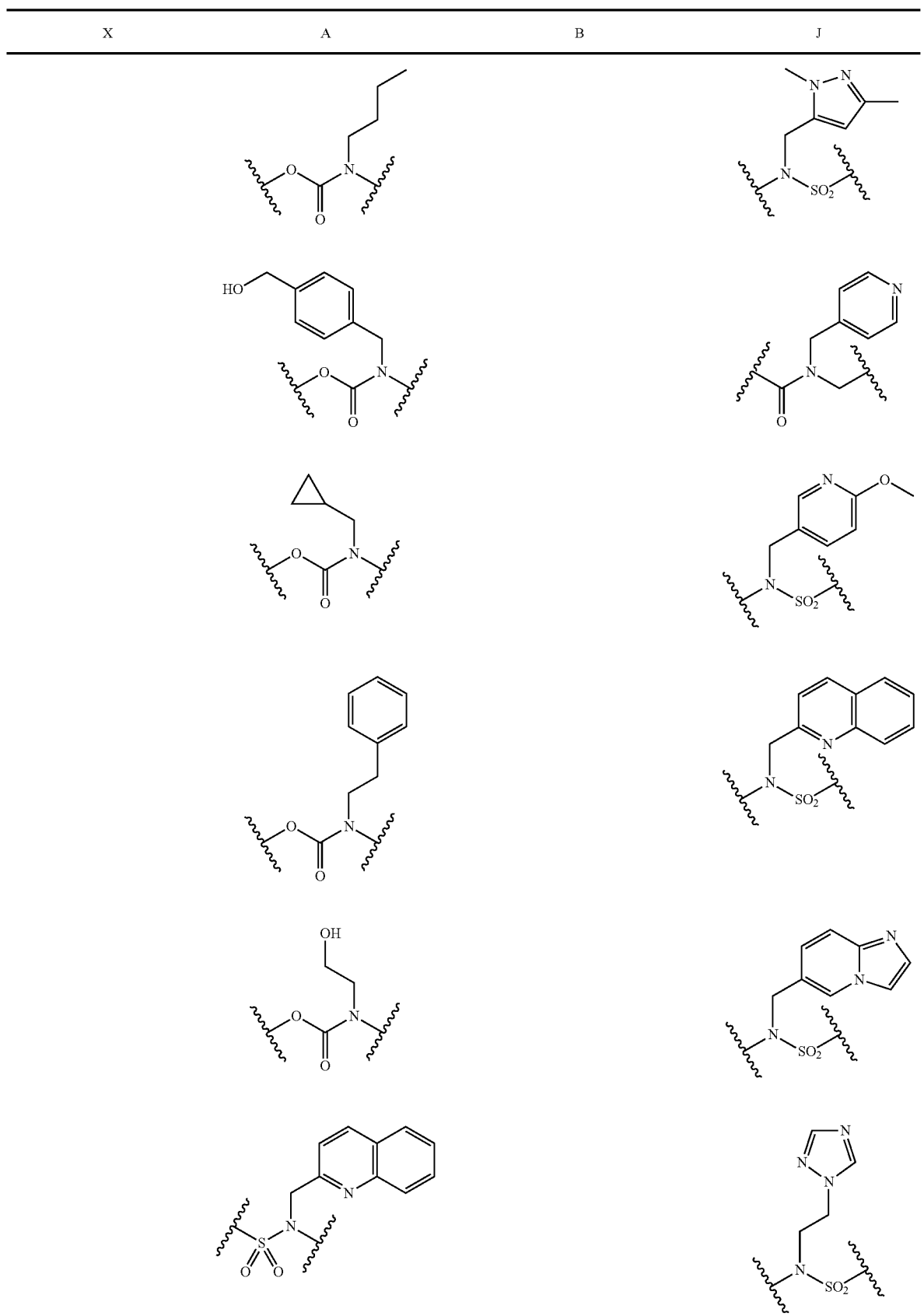

-continued

| X | A | B | J |
|---|---|---|---|

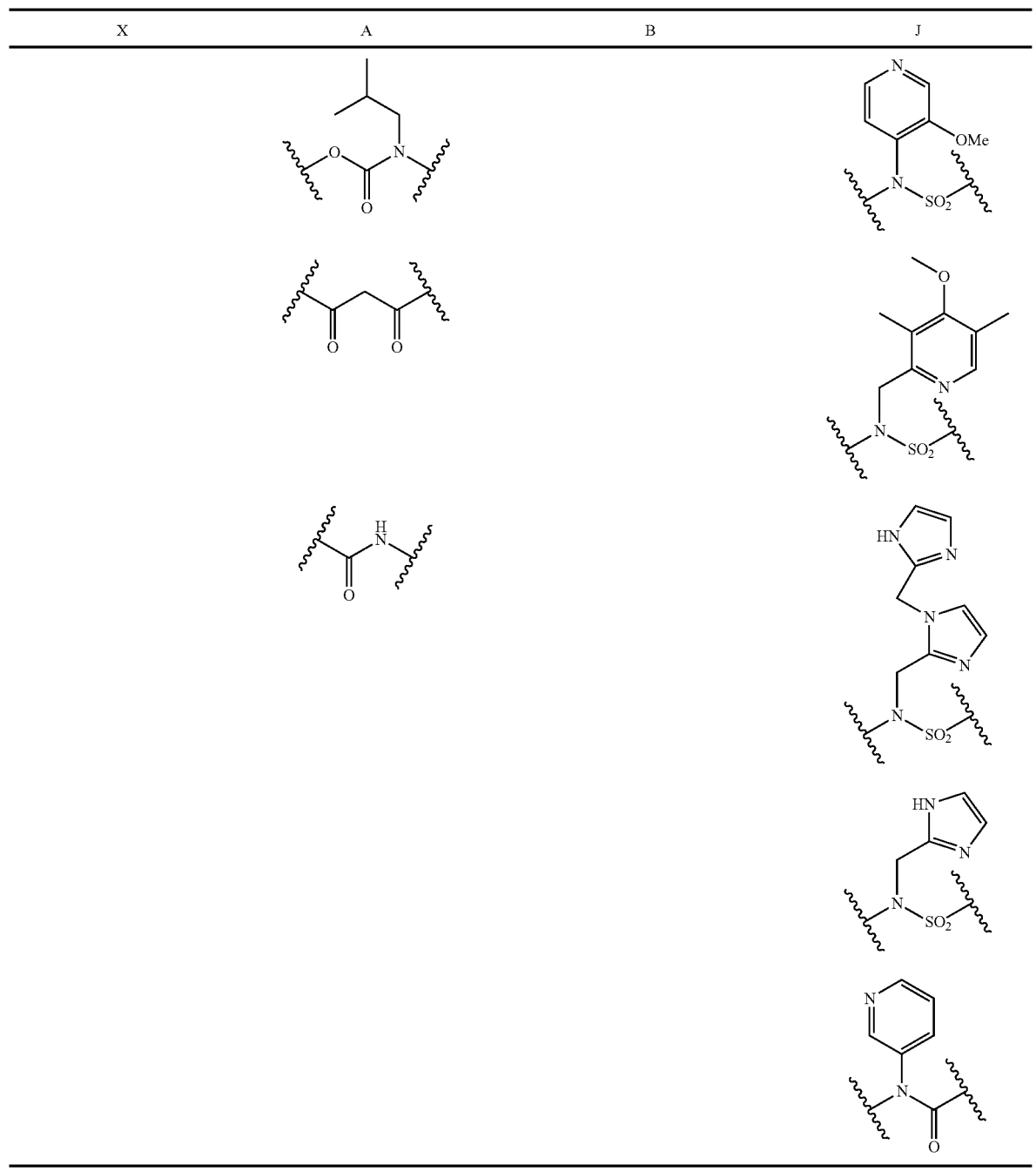

The term "pharmaceutically effective amount" also refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The term "antiretroviral agent" as used herein refers to a compound that inhibits the ability of a retrovirus to effectively infect a host. Antiretroviral agents can inhibit a variety of process including the replication of viral genetic materials, or entry of retroviruses into cells. In some embodiments, antiretroviral agents are selected from the group consisting of: protease inhibitor, a reverse transcriptase inhibitor, and a viral fusion inhibitor. In other embodiments the antiretroviral agents are selected from the group consisting of abacavir, didanosine, emtricitabine, lamivudine, stavudine, tenofovir, zidovudine, elvucitabine, apricitabine, zalcitabine, delavirdine, efavirenz, nevirapine, rilpivirine, etravirine, atazanavir, darunavir, fosamprenavir, indinavir, lopinavir, Kaletra, nelfinavir, ritonavir, saquinavir, tipranavir, enfuvirtide, maraviroc, vicriviroc, raltegravir, elvitegravir, interferon, albuferon, telaprevir, boceprevir, and viramidine.

The term "lipophilic group" as used herein refers to a group that, when a part of a compound, increases the affinity or propensity of the compound to bind, attach or dissolve in fat, lipid or oil rather than water. A measure of the lipophilicity or hydrophobicity of compounds of the technology can be calculated using the Hansch equation:

$$\text{Log } 1/C = kP$$

where C is the concentration of a compound in a given solvent and P is the hydrophobicity. Details of this method can be obtained from *J. Amer. Chem. Soc*, 86:5175 (1964) and *Drug Design I*, edited by E. J. Ariens, Academic Press (1971), both of which are hereby incorporated by reference in their entireties.

Examples of a typical lipophilic group include, but are not limited to, alkyl groups such as methyl, ethyl, n-propyl, isopropyl, n-butyl, isobutyl, t-butyl, n-pentyl, isopentyl, neopentyl, amyl, n-hexyl, n-heptyl, cyclohexyl, cycloheptyl, octyl, nonyl, decyl, undecyl, and dodecyl, alkenes such as ethylene, propylene, butene, pentene, hexene, cyclohexene, heptene, cycloheptene, octene, cyclooctene, nonene, decene, undecene, dodecene, 1,3-butadiene, alkynes such as propyne and butyne, aryls such as phenyl, naphthyl, anthracenyl, phenanthrenyl, fluorenyl, aralkyls such as benzyl, heterocyclyls such as tetrahydrothiophene, dihydrobenzofuran, heteroaryls such as pyrrole, furan, thiophene, pyrazole, thiazole, indole, carbazole, benzofuran, benzothiophene, indazole, benzothiazole, purine, pyridine, pyridazine, pyrazine, triazine, quinoline, acridine, isoquinoline, and phenanthroline.

For small groups containing heteroatom substituents, such as small heterocycles with a high ratio of heteroatoms to carbon atoms, the introduction of substituents that reduce the heteroatom to carbon atom ratio renders the group lipophilic. For example, a triazole ring can be rendered more lipophilic by the introduction of alkyl substituents. Similarly, non-lipophilic substituents such as hydroxy or amido can be rendered lipophilic by introducing additional carbon atoms, for example by exchanging a hydroxymethyl group to a hydroxybenzyl group, or by exchanging a carboxamido group to a dialkyl carboxamido group.

A 'resistance-repellent' protease inhibitor ("PI") is a compound that retains inhibitory activity, or potency, over a broad spectrum of related but non-identical retroviral proteases. Examples of resistance-repellent PIs include, but are not limited to, PIs that inhibit wild type HIV-1 protease derived from any Glade B virus and 1) a wild type retroviral protease from one or more different retroviruses, such as HIV-2 protease; or 2) mutant HIV-1 proteases with single active site mutations at residues 30, 82 and 84; or 3) mutant HIV-1 proteases with single active site mutations at residues 47, 48, and 50; or 4) mutant HIV-1 proteases with double active site mutations at residues 82 and 84; or 5) mutant HIV-1 proteases with double active site mutations at residues 47 and 48, 47 and 50, or 48 and 50; or 6) mutant HIV-1 proteases with double active site mutations at residues 48 and 82, 48 and 90, or 82 and 90; or 7) mutant HIV-1 proteases with three or more active site mutations in any combination at residues 32, 47, 48, 50, 82, 84 or 90.

The term "substituted", whether preceded by the term "optionally" or not, and substitutions contained in formulas of this technology, include the replacement of one or more hydrogen radicals in a given structure with the radical of a specified substituent.

When more than one position in a given structure can be substituted with more than one substituent selected from a specified group, the substituents can be either the same or different at every position (for example, in the moiety —N(R)$_2$, the two R substituents can be the same or different). In those embodiments where a structure can be optionally substituted, any or all of the hydrogens present may be replaced by substituents. In some embodiments, 0-3 hydrogen atoms may be replaced. In other embodiments, 0 or 1 hydrogen atoms may be replaced. Substituents advantageously enhance cytochrome P450 inhibitory activity in permissive mammalian cells, or enhance deliverability by improving solubility characteristics or pharmacokinetic or pharmacodynamic profiles as compared to the unsubstituted compound. Enhancements to cytochrome P450 inhibitory activity, deliverability and pharmacokinetic parameters achieved by the addition of substituents may result in synergistic enhancement of a compound's action and suitability for use in one or more applications.

Combinations of substituents and variables envisioned by this technology are limited to those that result in the formation of stable compounds. The term "stable", as used herein, refers to compounds which possess stability sufficient to allow manufacture, formulation, and administration to a mammal by methods known in the art. Typically, such compounds are stable at a temperature of 40° C. or less, in the absence of moisture or other chemically reactive conditions, for at least a week. In one embodiment, the compounds have less than 5% degradation after storage in the dark at 40° C. or less, in the absence of moisture or other chemically reactive conditions. In another embodiment compounds have less than 10% degradation after storage in the dark at 40° C. or less, in the absence of moisture or other chemically reactive conditions.

The term "alkyl", alone or in combination with any other term, refers to a straight-chain or branched-chain saturated aliphatic hydrocarbon radical containing the specified number of carbon atoms, or where no number is specified, advantageously from 1 to about 12 or 1 to 15 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, advantageously from 2-6 or 2-10 carbon atoms. Alkenyl groups include all possible E and Z isomers unless specifically stated otherwise. Examples of alkenyl radicals include, but are not limited to, ethenyl, propenyl, isopropenyl, butenyl, isobutenyl, pentenyl, hexenyl, hexadienyl and the like.

The term "alkynyl," alone or in combination with any other term, refers to a straight-chain or branched-chain hydrocarbon radical having one or more triple bonds containing the specified number of carbon atoms, or where no number is specified, advantageously from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, where the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The terms "alkylamino" or "dialkylamino" include amino radicals substituted by one or two alkyl groups, where the term "alkyl" is defined above, and the alkyl groups can be the same or different. Examples of suitable alkylamino and dialkylamino radicals include, but are not limited to, methylamino, ethylamino, isoproyplamino, dimethylamino, methylethylamino, ethylbutylamino and the like.

The term "hydroxyalkyl" refers to an alkyl radical as defined above in which one of the hydrogen atoms is replaced by hydroxy group. Examples of suitable hydroxyalkyl radicals include, but are not limited to, hydroxymethyl, 2-hydroxypropyl and the like.

The term "alkoxyalkyl" refers to an alkyl radical as defined above in which one of the hydrogen atoms is replaced by an alkoxy radical as defined above.

The terms "aminoalkyl", "alkylaminoalkyl" or "dialkylaminoalkyl" refers to an alkyl radical as defined above in which one of the hydrogen atoms is replaced by an amino or "alkylamino" or "dialkylamino" radical as defined above.

The term "halo" or "halogen" includes fluorine, chlorine, bromine or iodine. Halo may be limited to fluorine, chlorine, and bromine or fluorine and chlorine.

The term "haloalkyl" includes alkyl groups with one or more hydrogens replaced by halogens.

The term "thioalkyl" includes alkyl radicals having at least one sulfur atom, where alkyl has the significance given above. An example of a thioalkyl is $CH_3SCH_2$—. The definition also encompasses the corresponding sulfoxide and sulfone of this thioalkyl $CH_3S(O)CH_2$— and $CH_3S(O)_2CH_2$— respectively. Unless expressly stated to the contrary, the terms "—$SO_2$—" and "—$S(O)_2$—" as used herein include sulfones or sulfone derivatives (i.e., both appended groups linked to the S), and not a sulfinate ester.

The terms "carboalkoxy" or "alkoxycarbonyl" include alkyl esters of a carboxylic acid. Examples of "carboalkoxy" or "alkoxycarbonyl" radicals include, but are not limited to, ethoxycarbonyl (or carboethoxy), Boc (or t-butoxycarbonyl), Cbz (or benzyloxycarbonyl) and the like.

The term "alkanoyl" includes acyl radicals derived from an alkanecarboxylic acid. Examples of alkanoyl radicals include, but are not limited to acetyl, propionyl, isobutyryl and the like.

The term "aryl," alone or in combination with any other term, refers to a carbocyclic aromatic radical (such as phenyl or naphthyl) containing a specified number of carbon atoms. In some embodiments, aryl radicals contain from 6-16 carbon atoms, and in other embodiments aryl radicals contain from 6 to 14 or 6-10 carbon atoms in their ring structures. Aryl radicals may be optionally substituted with one or more substituents selected from alkyl, alkoxy, (for example methoxy), nitro, halo, amino, mono or dialkylamino, carboalkoxy, cyano, thioalkyl, alkanoyl, carboxylate, and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, includes alkyl radicals as defined above in which one or more hydrogen atoms is replaced by an aryl radical as defined above. Examples of aralkyl radicals include, but are not limited to benzyl, 2-phenylethyl and the like.

The term "carbocycle" refers to a non-aromatic, stable 3- to 8-membered carbon ring which can be saturated, mono-unsaturated or poly-unsaturated. The carbocycle can be attached at any endocyclic carbon atom which results in a stable structure. In some embodiments, carbocycles having 5-7 carbons may be employed, whereas in other embodiments, carbocycles having 5 or 6 carbon atoms may be employed.

The term "cycloalkyl", alone or in combination, includes alkyl radicals which contain from about 3 to about 8 carbon atoms and are cyclic. Examples of such cycloalkyl radicals include cyclopropyl, cyclobutyl, cyclopentyl, cyclohexyl and the like.

The term "cycloalkenyl" alone or in combination includes alkenyl radicals as defined above which contain about 3-8 carbon atoms and are cyclic.

In some embodiments of carbocycles, cycloalkyl or cycloalkenyl groups contain 3 or 4 carbon atoms in their ring structure. In other embodiments of carbocycles, cycloalkyl or cycloalkenyl groups contain 5 or 6 carbon atoms in their ring structure. In still other embodiments of carbocycles, cycloalkyl or cycloalkenyl groups contain 7 or 8 carbon atoms in their ring structure.

The term "cycloalkylalkyl" includes alkyl radicals as defined above which are substituted by a cycloalkyl radical containing from about 3 to about 8 carbon atoms in some embodiments, or from about 3 to about 6 carbon atoms in other embodiments.

The term "heterocyclyl" or "heterocyclo" or "heterocycloalkyl" refers to a stable 3-7 membered monocyclic heterocycle or 8-11 membered bicyclic heterocycle which is either saturated or partially unsaturated, and which can be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include oxidized forms of nitrogen and sulfur, and the quaternized form of any basic nitrogen. A heterocyclyl radical can be attached at any endocyclic carbon or heteroatom which results in the creation of a stable structure. Preferred heterocycles include 5-7 membered monocyclic heterocycles, and 8-10 membered bicyclic heterocycles. Examples of such groups are imidazolinyl, imidazolidinyl, indazolinyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "heteroaryl" refers to stable 5-6 membered monocyclic or 8-11 membered bicyclic or 13-16 membered tricyclic aromatic heterocycles where heterocycle is as defined above. In some embodiments, heteroatoms present in heteroaryl radicals are limited to one or more independently selected O, N or S atoms. Non-limiting examples of such groups include imidazolyl, quinolyl, isoquinolyl, indolyl, indazolyl, pyridazyl, pyridyl, pyrrolyl, pyrazolyl, pyrazinyl, quinoxalinyl, pyrimidinyl, furyl, thienyl, triazolyl, thiazolyl, carbolinyl, tetrazolyl, benzofuranyl, oxazolyl, benzoxazolyl, benzimidazolyl, benzthiazolyl, isoxazolyl, isothiazolyl, furazanyl, thiadiazyl, acridinyl, phenanthridinyl, and benzocinnolinyl.

The term "heterocycloalkylalkyl" refers to an alkyl radical as defined above which is substituted by a heterocycloalkyl radical as defined above.

The term "heteroaralkyl" alone or in combination, includes alkyl radicals as defined above in which one or more hydrogen atom is replaced by a hetoroaryl group as defined above.

As used herein, the compounds of this technology are defined to include pharmaceutically acceptable derivatives or prodrugs thereof. A "pharmaceutically acceptable derivative or prodrug" includes a pharmaceutically acceptable salt, ester, salt of an ester, or other derivative of a compound of this technology which, upon administration to a recipient, is capable of providing (directly or indirectly) a compound of this technology. Particularly favored derivatives and prodrugs are those that increase the bioavailability of the compounds of this technology when such compounds are administered to a mammal (e.g., by allowing an orally administered compound to be more readily absorbed into the blood) or which enhance delivery of the parent compound to a biological compartment (e.g., the brain or lymphatic system) relative to the parent species. Examples of prodrugs of hydroxy containing compounds are amino acid esters or phosphonate or phosphate esters that can be cleaved in vivo hydrolytically or enzymatically to provide the parent compound. These have the advantage of providing potentially improved solubility.

Resistance-repellent PIs should generally also retain inhibitory activity, or potency, over a broad spectrum of related but non-identical retroviruses. In particular, resistance-repellent PIs should inhibit all HIV-1 virus strains that contain a gene sequence of the protease region of the HIV-1 pol gene that is typified by one or more 'wild type' strains derived from Glade B and: 1) HIV-1 virus strains that contain a gene sequence of the protease region of the HIV-1 pol gene derived from wild type, non-Glade B viruses; or 2) wild type HIV-2 virus strains; or 3) HIV-1 virus strains derived from patients who are infected with HIV-1 that contain mutations in the protease gene.

The compounds of formula (I) can contain one or more asymmetric carbon atoms and thus occur as racemates and racemic mixtures, single enantiomers, diastereomeric mixtures and individual diastereomers. All such isomeric forms of these compounds are expressly included in the technology described herein. Each stereogenic carbon can be of the R or S configuration. Although the specific compounds exemplified in this application can be depicted in a particular stereochemical configuration, compounds having either the opposite stereochemistry at any given chiral center or mixtures thereof are also envisioned. Thus, the compounds provided herein may be enantiomerically pure, or be stereoisomeric or diastereomeric mixtures.

In the case of amino acid residues, such residues may be of either the L- or D-form. The configuration for naturally occurring amino acid residues is generally L. When not specified the residue is the L form. As used herein, the term "amino acid" refers to α-amino acids which are racemic or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo.

As such, one of skill in the art will recognize that administration of a compound in its (R) form is equivalent, for compounds that undergo epimerization in vivo, to administration of the compound in its (S) form.

It is also to be understood that the compounds provided herein may have tautomeric forms. All such tautomeric forms are included within the scope of the instant disclosure. For example, a 3-enamino-2-oxindole where the amino group of the enamine has a hydrogen substituent has the tautomeric form of a 3-imino-2-hydroxyindole.

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorph or polymorph mixtures are included in the present application.

Preparation and Assay of the Compounds

The compounds can be prepared according to synthetic methods known in the art set forth, for example, in U.S. Pat. No. 6,319,946 to Hale et al., WO2008022345A2 (Eissenstat et al.), and in *J. Med. Chem.* 36: 288-291 (1993), the disclosures of which are incorporated herein by reference in their entireties, together with procedures of the type described below. Reactions and processes for obtaining the compounds, particularly the formation of ester and amide linkages, may also be found in treatises and text, including, but not limited to, Advanced Organic Synthesis, 4th Edition, J. March, John Wiley & Sons, 1992 or Protective Groups in Organic Synthesis 3rd Edition, T. W. Green & P. G. M. Wuts, John Wiley & Sons, 1999, each of which is hereby incorporated by reference.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's *Reagents for Organic Syntheses*, Volumes 1-85 (John Wiley and Sons); Rodd's *Chemistry of Carbon Compounds*, Volumes 1-5 and Supplementals (Elsevier Science Publishers, 1989); *Organic Reactions*, Volumes 1-71 (John Wiley and Sons), *Advanced Organic Synthesis*, 4th Edition, J. March, John Wiley & Sons, 1992, and Larock's *Comprehensive Organic Transformations* (VCH Publishers Inc., 1989).

Protective groups, such as those described in *Protective Groups in Organic Synthesis* 3rd Edition, T. W. Green & P. G. M. Wuts, John Wiley & Sons, 1999 may be employed for a variety of purposes in the preparation of compounds encompassed by this disclosure. They may be employed to control the number or placement of substituents, or to protect functionalities that are otherwise unstable to reaction conditions employed for the introduction or modification of other substituents in a molecule. Where employed, such protective groups may be removed by suitable means. Alternatively, where the protective group is desirable in the product they may be introduced and not removed.

Assessment of Compounds

The potency of the compounds can be measured using assays, for example, an in vitro fluorometric assay. Typically, the ability of a test compound to inhibit P450 is assayed by determining the concentration of the test compound required to decrease the maximal rate of metabolism of a CYP substrate (also referred to herein as reference compound) by half. The CYP substrate can be, for example, dibenzylfluorescein. The ability of a test compound to inhibit the maximal rate of metabolism of a reference compound by half is known as the $IC_{50}$ value. Human liver microsomes can be used for this purpose. Test compounds can be diluted with a suitable solvent, such as acetonitrile, in wells of a microtiter plate. Known cytochrome P450 inhibitors such as ritonavir and ketoconazole can be used as references. A suitable buffer solution and a NADPH generating system such as, for example, G6P dehydrogenase can be used. After mixing the inhibitors with the buffer and NADPH system, the plates can be incubated for a suitable time at a suitable temperature. A solution containing human liver microsomes can be added. A buffer containing a fluorogenic substrate, such as dibenzylfluorescein, can be added and the plates allowed to incubate for a suitable time at a suitable temperature. The $IC_{50}$ values for the test compounds can be measured by determining the amount of fluorescence in each well and analyzing the values using commercially available software programs such as, for example, Grafit® (Erithacus Software Ltd., Surrey, U.K.).

In certain embodiments, there is disclosed a method for improving the pharmacokinetics of an HIV protease inhibitor (or a pharmaceutically acceptable salt thereof) which is metabolized by cytochrome P450 monooxygenase including coadministering a compound of the technology or a pharmaceutically acceptable salt thereof. Such a combination of a compound of the technology or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be administered as a single composition.

Methods of Administration

The compounds of this technology may be administered to an uninfected or HIV-infected patient either as a single agent or in combination therapy with other anti-viral agents that interfere with the replication cycle of HIV in order to increase the therapeutic effect of these compounds. Thus, the present technology also relates to compositions including a compound of the present technology, and another antiretroviral compound as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (ADS) or AIDS Related Complex (ARC), the compounds of this technology may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-Ji; co-receptor binding inhibitors, such as, for example, AMD 3100, AMD-3465, AMD7049, AMD3451 (Bicyclams), TAK 779; SHC-C (SCH351125), SHC-D, PRO-140RT inhibitors, such as, for example, foscarnet and prodrugs; nucleoside RTIs, such as, for example, AZT, 3TC, DDC, DD1, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPC082, DPC083, calanolide A, SJ-1366, TSAO, 4"-deaminated TSAO, MVI50, MV026048; RNAse H inhibitors, such as, for example, SPI093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, .BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMCl14, maslinic acid, U-140690; glycosylation inhibitors, such as, for example, castanospermine, deoxynojirimycine.

In some embodiment the compounds of this technology may be administered to an uninfected or HIV-infected patient along with a HIV protease inhibitor such as: A-77003, A-80987, indinavir, saquinavir, amprenavir, nelfinavir, fosamprenavir, lopinavir, atazanavir, darunavir, tipranavir, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), PPL-100, SPI-256 or KNI-272. In embodiments, the drug may be inhibitors of CD4-gp120 interaction, CCR5 and CRCX4 coreceptors, or inhibitors of the LEDGF-integrase interaction.

The combination may in some cases provide a synergistic effect, whereby viral infectivity and its associated symptoms may be prevented, substantially reduced, or eliminated completely.

The compounds of the present technology may also be administered in combination with immunomodulators (e.g., bropirimine, anti-human alpha interferon antibody, IL-2, methionine enkephalin, interferon alpha, 1-1E-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIM infection and its symptoms.

Such combination therapy in different formulations may be administered simultaneously, separately or sequentially. Alternatively, such combination may be administered as a single formulation, whereby the active ingredients are released from the formulation simultaneously or separately.

The compounds of the technology can be administered in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Other pharmaceutically acceptable salts include salts with an inorganic base, organic base, inorganic acid, organic acid, or basic or acidic amino acid. Inorganic bases which form pharmaceutically acceptable salts include alkali metals such as sodium or potassium, alkali earth metals such as calcium and magnesium, aluminum, and ammonia. Organic bases which form pharmaceutically acceptable salts include trimethylamine, triethylamine, pyridine, picoline, ethanolamine, diethanolamine, triethanolamine, dicyclohexylamine. Inorganic acids which form pharmaceutically acceptable salts include hydrochloric acid, hydroboric acid, nitric acid, sulfuric acid, and phosphoric acid. Organic acids appropriate to form salts include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids used to form salts include arginine, lysine and ornithine. Acidic amino acids used to form salts include aspartic acid and glutamic acid.

The CYP inhibitory compounds described herein may be prepared and administered as a composition comprising a co-crystals with other compounds (co-crystal fomers). "Co-crystal" as used herein means a crystalline material comprised of two or more unique solids at room temperature, each containing distinctive physical characteristics, such as structure, melting point and heats of fusion. Co-crystals are described, for example, in U.S. Pub. No.: 20070026078 A1, which is incorporated by reference in its entirety. They are also described in, N. A. Meanwell, Annual Reports in Medicinal Chemistry, Volume 43, 2008 and D. P. McNamara, Pharmaceutical Research, Vol. 23, No. 8, 2006, each of which is incorporated by reference in its entirety.

The technology also contemplates compositions which can be administered orally or non-orally in the form of, for example, granules, powders, tablets, capsules, syrup, suppositories, injections, emulsions, elixirs, suspensions or solutions, by mixing these effective components, individually or simultaneously, with pharmaceutically acceptable carriers, excipients, binders, diluents or the like.

As a solid formulation for oral administration, the composition can be in the form of powders, granules, tablets, pills and capsules. In these cases, the compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

Examples of liquid preparations for oral administration include pharmaceutically acceptable emulsions, syrups, elixirs, suspensions and solutions, which can contain an inactive diluent, for example, water.

As used herein, "non-orally" includes subcutaneous injection, intravenous injection, intramuscular injection, intraperitoneal injection or instillation. Injectable preparations, for example sterile injectable aqueous suspensions or oil suspensions, can be prepared by known procedures in the fields concerned, using a suitable dispersant or wetting agent and suspending agent. The sterile injections can be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The pharmaceutical compositions can be formulated for nasal aerosol or inhalation and can be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

The pharmaceutical composition can be easily formulated for topical administration with a suitable ointment containing one or more of the compounds suspended or dissolved in a carrier, which include mineral oil, liquid petroleum, white petroleum, propylene glycol, polyoxyethylene, polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetaryl alcohol, 2-octyldodecanol, benzyl alcohol and water.

In some embodiments, the pharmaceutical compositions can include α-, β-, or γ-cyclodextrins or their derivatives. In certain embodiments, co-solvents such as alcohols can improve the solubility and/or the stability of the compounds in pharmaceutical compositions. In the preparation of aqueous compositions, addition salts of the compounds can be suitable due to their increased water solubility.

Appropriate cyclodextrins are α-, β-, or γ-cyclodextrins (CDs) or ethers and mixed ethers thereof where one or more of the hydroxy groups of the anhydroglucose units of the cyclodextrin are substituted with $C_1$-$C_6$alkyl, such as methyl, ethyl or isopropyl, e.g. randomly methylated β-CD; hydroxy $C_{1-6}$alkyl, particularly hydroxyethyl, hydroxypropyl or hydroxybutyl; carboxy $C_1$-$C_6$alkyl, particularly carboxymethyl or carboxyethyl; $C_1$-$C_6$alkyl-carbonyl, particularly acetyl; $C_1$-$C_6$alkyloxycarbonyl$C_1$-$C_6$alkyl or carboxy$C_1$-$C_6$alkyloxy$C_1$-$C_6$alkyl, particularly carboxymethoxypropyl or carboxyethoxypropyl; $C_1$-$C_6$alkylcarbonyloxy$C_1$-$C_6$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxypropyl-γ-CD and (2-carboxymethoxy)propyl-β-CD, and in particular 2-hydroxypropyl-β-CD (2-HP-β-CD).

The term "mixed ether" denotes cyclodextrin derivatives where at least two cyclodextrin hydroxy groups are etherified with different groups such as, for example, hydroxypropyl and hydroxyethyl.

The compounds can be formulated in combination with a cyclodextrin or a derivative thereof as described in U.S. Pat. No. 5,707,975. Although the formulations described therein are with antifungal active ingredients, they are equally relevant for formulating compounds and compositions of the technology described herein (e.g., compositions comprising a compound of formula I and a compound of formula II). The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations can also be rendered more palatable by adding pharmaceutically acceptable sweeteners and/or flavors.

Other convenient ways to enhance the solubility of the compounds of the technology in pharmaceutical compositions are described in WO 94/05263, WO 98/42318, EP-A-499,299 and WO 97/44014, all incorporated herein by reference.

In some embodiments, the compounds can be formulated in a pharmaceutical composition including a therapeutically effective amount of particles consisting of a solid dispersion including a compound of formula I, and one or more pharmaceutically acceptable water-soluble polymers.

The term "solid dispersion" defines a system in a solid state including at least two components, where one component is dispersed more or less evenly throughout the other component or components. When the dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It can further be convenient to formulate the compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The compounds can also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration can depend on the condition of the subject, co-medication and the like.

Dosages of the compounds and compositions described herein are dependent on age, body weight, general health conditions, sex, diet, dose interval, administration routes, excretion rate, combinations of drugs and conditions of the diseases treated, while taking these and other necessary factors into consideration. Generally, dosage levels of between about 10 µg per day to about 5000 mg per day, preferably between about 25 mg to about 1000 mg administered at periodic intervals are useful for the inhibition of CYP enzymes. Typically, the pharmaceutical compositions of this technology will be administered from about 1 to about 3 times per day or alternatively, as a continuous infusion. Alternatively, sustained release formulations, may be employed. Sustained release formulations include, but not limited to, trans-dermal or iontophoretic patches, osmoitic devices, or sustained release tablets or suppositories that generally employ expandable or erodible polymer compositions. Such administrations can be used as a chronic or acute therapy.

The amount of active ingredient(s) that can be combined with the carrier materials to produce a single dosage form will vary depending upon the host treated and the particular mode of administration. A typical preparation will contain from about 5% to about 95% active compound (w/w). In some embodiments, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 5% to about 95% active compound (w/w). Preferably, such preparations contain from about 10% to about 80% active compound. The desired unit dose of the composition of this technology is administered once or multiple times daily.

In some embodiments, the technology contemplates compositions and formulations including one or more of the compounds in combination with one or more other drugs that can be metabolized or degraded by CYP.

The CYP inhibitors of this technology can be administered to a patient either as a single agent (for use with a separate dose of another drug) or in a combined dosage form with at least one other drug. Additional drugs also can be used to increase the therapeutic effect of these compounds.

The compounds of this technology can be administered to patients being treated with a drug that is metabolized by a CYP enzyme. Such drugs include, but are not limited to, anesthetics such as ropivacaine, enflurane, halothane, isoflurane, methoxyflurane, and sevoflurane; antiarrhythmics such as mexiletine; antidepressants such as amitriptyline, clomipramine, fluvoxamine, bupropion, and imipramine; anti-epileptics such as diazepam, phenyloin, S-mephenyloin, and phenobarbitone; antihistamines such as astemizole, chlorpheniramine, and terfenidine; antipsychotics such as clozapine, olanzapine, and haloperidol; beta blockers such as carvedilol, S-metoprolol, propafenone, and timolol; calcium channel blockers such as amlodipine, diltiazem, felodipine, lercanidipine, nifedipine, nisoldipine, nitrendipine, and verapamil; hypoglycemic agents such as tolbutamide and glipizide; immune modulators such as cyclosporine and tacrolimus; muscle relaxants such as cyclobenzaprine, tizanidine, and carisoprodol; steroids such as estradiol; antimigraine agents such as zolmitriptan; agents used to treat breathing aliments such as zileuton and theophylline; agents used to treat Alzheimer's disease such as tacrine; agents used to treat pain such as naproxen and acetaminophen; agents used to treat amyotrophic lateral sclerosis such as riluzole; anti-nausea agents such as ondansetron; chemotherapeutics such as paclitaxel, ifosfamide, and cyclophosphamide; loop diuretics such as torsemide; antidiabetic agents such as repaglinide; statin such as cerivastatin; antimalarial agents such as amodiaquine; proton pump inhibitors such as lansoprazole, omeprazole, pantoprazole, and rabeprazole; and sulfonylureas such as glyburide, glibenclamide, glipizide, glimepiride, and tolbutamide. Patients being treated with a protease inhibitor, a reverse transcriptase inhibitor, a viral fusion inhibitor, or an integrase inhibitor can also be treated with the compounds provided herein. The CYP inhibitors provided herein can be co-administered with the other drug(s). The compounds of the technology can also be administered in combination with other cytochrome P450 inhibitors (e.g., ritonavir), immuno-modulators (e.g., bropirimine, anti-human alpha interferon antibody, IL-2, interferon alpha, and HE-2000), with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate infections as therapeutically appropriate.

CYP inhibitors can also be used as standalone therapeutics for CYP-mediated diseases, or as prophylactic agents for preventing the production of toxic metabolites. For example, an inhibitor of CYP2A6 or 2A 13 can be used to ameliorate the carcinogenic effects of tobacco usage.

Such combination therapy in different formulations can be administered simultaneously, separately or sequentially. The CYP inhibitors can be administered prior to administration of the other drug to reduce CYP levels and minimize degradation of the drug. In specific embodiments, the CYP inhibitor is administered, 30 minutes, 1 hour, four hours, twelve hours or twenty four hours prior to initial administration of the other drug. The CYP inhibitors tend to have a long half in vivo, presumably as a result of inhibiting their own metabolism. This means that once treatment has begun, the CYP inhibitor may be administered less frequently than the drug, although the skilled artisan will recognize that different administration regiments may be needed in specific situations. In certain instances, CYP inhibitors can also induce expression of CYPs and the skilled artisan will appreciate that in such circumstances, administration of the CYP inhibitor may need to be more frequent. Alternatively, such combinations can be administered as a single formulation, whereby the active ingredients are released from the formulation simultaneously or separately.

The following examples illustrate further the technology but, of course, should not be construed in any way of limiting its scope.

EXAMPLES

Example 1

Assay of $IC_{50}$ for CYP Inhibitors: Determinations Using Dibenzylfluorescein Metabolism by Human Liver Microsomes A microtiter plate based, fluorometric assay was used for the determination of the concentration of a test compound that will decrease by half the maximal rate of dibenzylfluorescein, a CYP3A4 substrate, metabolism by human liver microsomes. The assay was run as described by Crespi et al. Anal. Biochem. 248:188-90 (1997). Test compounds were diluted in acetonitrile in wells of a polypropylene microtiter plate (Denville Scientific, Inc. Metuchen, N.J.). Three fold serial dilutions of the test article were made from the first well into the next seven wells of a row. Two wells of each row were used for positive controls containing no test compound and two for negatives containing 500 µM Ritonavir in acetonitrile. Test compounds in acetonitrile (0.004 mL) were added to wells of a microtiter plate (Catalog No. 3598, Corning Costar, Cambridge, Mass.) containing a solution (0.096 mL) of 0.2 M KPO4 Buffer (pH 7.4) and a NADPH generating system (2.6 mM NADP, 6.6 mM glucose-6-phosphate, 3.3 mM MgCl2 and 0.8 Units/mL G6P dehydrogenase (BD/Gentest, Woburn, Mass.). The plates were incubated for 10 minutes at 37° C.

prior to addition of 0.1 mL of pre-warmed 0.1 mg/mL human liver microsomes (Xeno Tech, LLC, Lenexa, Kans.) in 0.2 M KPO4 buffer containing 2 µM dibenzylfluorescein (BD/Gentest, Woburn, Mass.). The plates were incubated for 10 minutes at 37° C. and the reaction are stopped by the addition of 0.075 mL of 2N NaOH. Plates were incubated at 37° C. for 1 hours prior to determining the amount of fluorescence in each well with a fluorescent plate reader (Spectra Max Gemini XS, Molecular Devices) at excitation/emission wavelengths of 485 and 538 nm (25 nm), respectively. Data were exported and analyzed using GraFit® (Erithacus Software Ltd., Surrey, U.K.). The background corrected data is fit to a 2-parameter equation for the determination of the $IC_{50}$.

Example 2

Synthetic Methods

The following experimental protocols are illustrative of the methods used to synthesize the cytochrome p450 inhibitors of the technology. Syntheses of the compounds below are exemplified, although the skilled artisan will recognize that these exemplary methods are of general applicability.

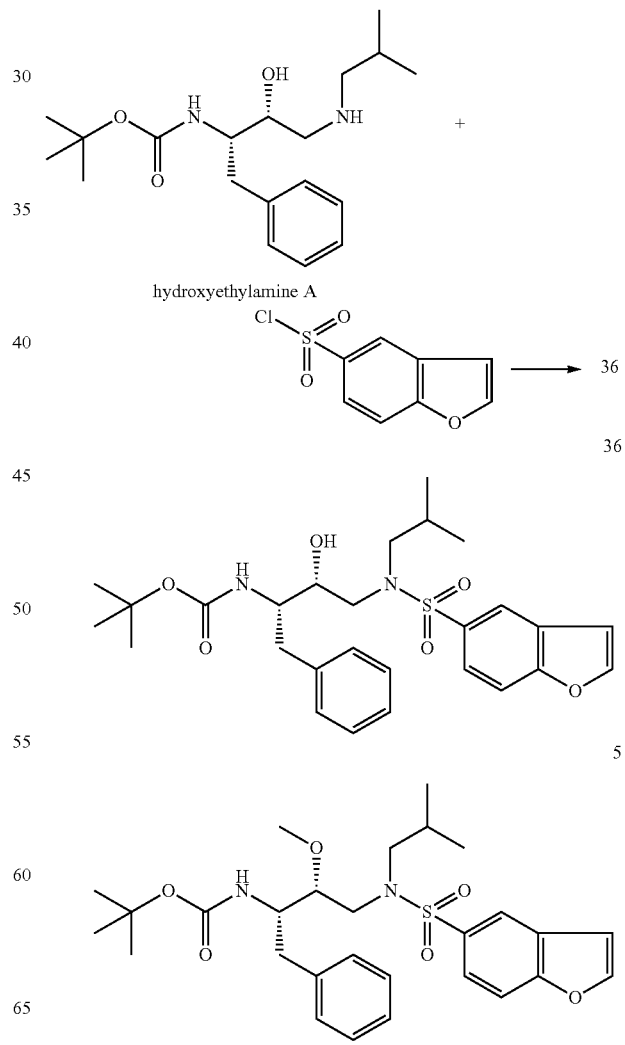

4

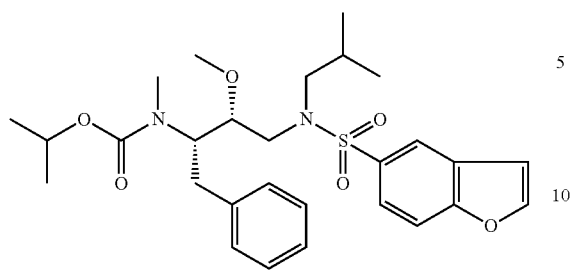

12

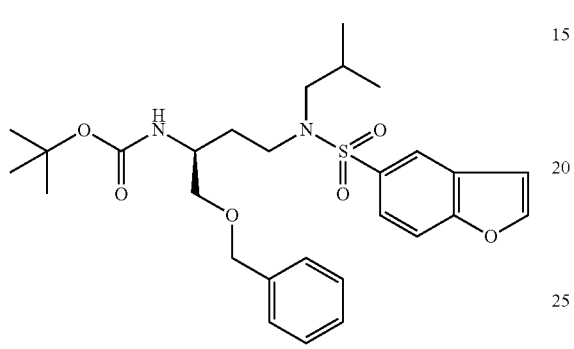

11

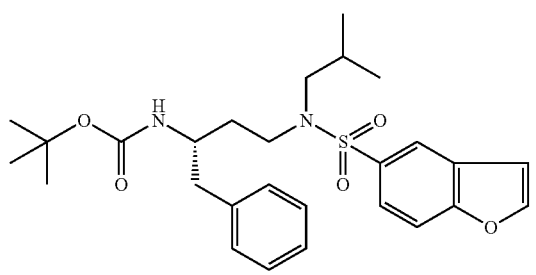

15

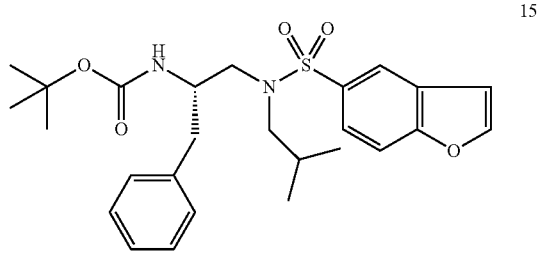

Example 2a

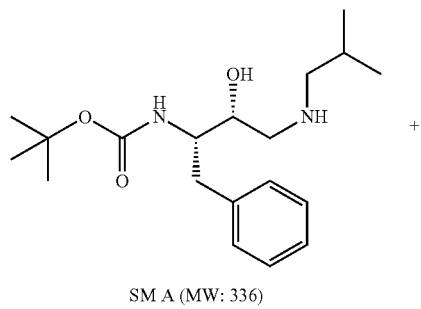

SM A (MW: 336)

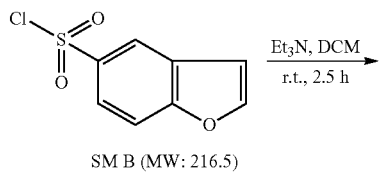

SM B (MW: 216.5)

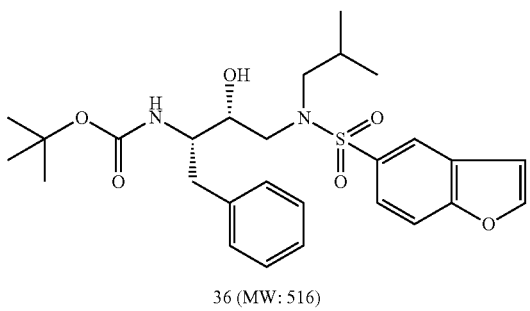

36 (MW: 516)

(1-Benzyl-2-hydroxy-3-isobutylamine-propyl)-carbamic acid tert-butyl ester (SM A, 10.08 g, 30 mmol, 1.0 equiv.) and 1-benzofuran-5-sulfonyl chloride (SM B, 9.74 g, 45 mmol, 1.5 equiv.) were dissolved in dichloromethane (100 mL). To the solution was added triethylamine (8.36 mL, 60 mmol, 2.0 equiv.) at room temperature. The mixture was stirred at the same temperature for 2.5 h, after which time the reaction was quenched through the addition of 0.5 N hydrochloric acid aqueous solution (50 mL). The phases were separated and then the organic layer was sequentially washed with 5% sodium bicarbonate (50 mL) and water (50 mL). The final organic solution was dried over anhydrous sodium sulfate and concentrated in vacuo. The residue was purified by recrystallization from ethyl acetate/hexane (30/90, v/v) to afford a white solid, 13.09 g, m.p. 121.1-122.4° C. The filtrate was concentrated and the residue was purified on silica gel (0-50% ethyl acetate in hexane) to afford 1.13 g additional target compound. Yield 14.22 g (92%). MS 1055 (2 MNa)$^+$, 539 (MNa)$^+$, 417 (M-BOC)$^+$ and 575 (AcOM)$^-$. Purity 97% (HPLC).

Example 2b

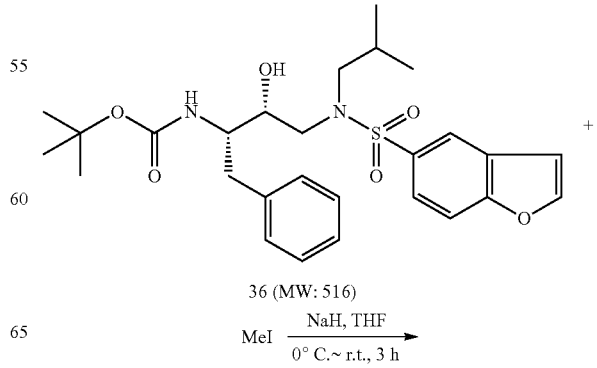

36 (MW: 516)

MeI $\xrightarrow[0° C. \sim r.t., 3 h]{NaH, THF}$

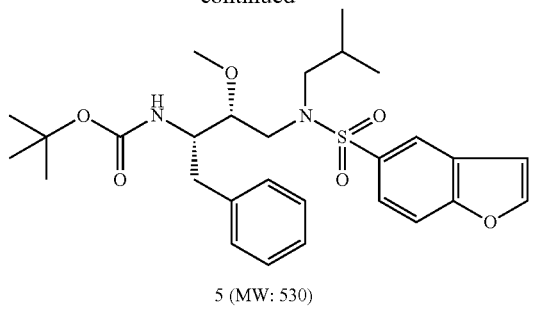

5 (MW: 530)

A 250 mL three-neck round-bottom flask was equipped with a magnetic stirbar, an argon inlet adapter and an air outlet adapter connected to a bubbler. The flask was charged with compound 36 (12.38 g, 24 mmol, 1.0 equiv.), anhydrous THF (96 mL), and methyl iodide (3.0 mL, 48 mmol, 2.0 equiv.) under argon. The mixture was cooled to 0° C. and treated with sodium hydride (1.92 g, 48 mmol, 2.0 equiv.) in portions. The resulting suspension was stirred for 3 h while the reaction was allowed to return to ambient temperature. Then 100 ml of water was added. The clear solution was concentrated in vacuo to remove the most of THF and was then extracted with ethyl acetate three times. The combined organic phase was washed with 0.5 N hydrochloric acid (50 mL), 5% sodium bicarbonate (50 mL), and brine (50 mL). It was then dried over anhydrous sodium sulfate and concentrated in vacuo to afford a yellow solid, which was purified by recrystallization from ethyl acetate/hexane (20/80, v/v) to afford a nearly colorless solid (9.15 g, 72%). A second recrystallization (ethyl acetate/hexane, 15/60) afforded a white solid (7.92 g), m.p. 115.3-115.8° C. $^1$H NMR ($\delta$, CDCl$_3$): 8.22 (s, 1H), 7.78-7.91 (m, 2H), 7.70 (d, J=8.4 Hz, 1H), 7.22-7.45 (m, 5H), 6.99 (s, 1H), 4.50-4.71 (m, 1H), 3.96-4.14 (m, 1H), 3.63-3.77 (m, 1H), 3.51 (s, 4H), 2.59-3.29 (m, 5H), 2.00-2.18 (m, 1H), 1.40 (s, 9H), 1.06 (d, J=6.4 Hz, 3H), 0.96 (d, J=6.4 Hz, 3H). MS 1083 (2 MNa)$^+$, 553 (MNa)$^+$, 431 (M-BOC)$^+$ and 589 (AcOM)$^-$. Purity 96% (HPLC).

Example 2c

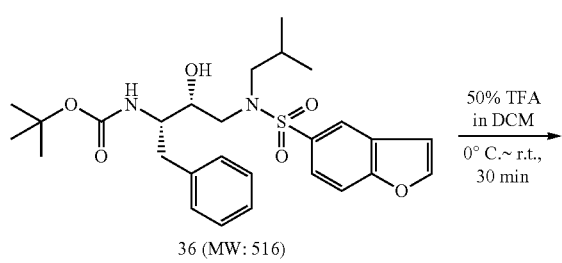

36 (MW: 516)

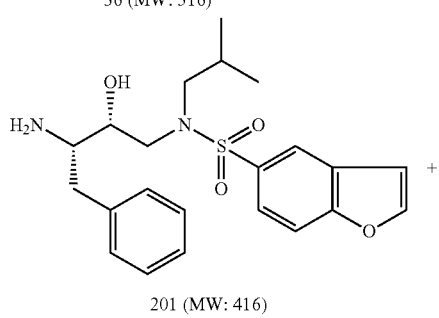

201 (MW: 416)

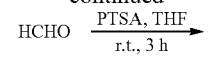

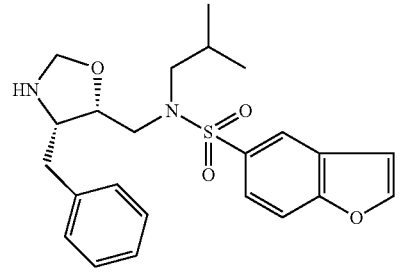

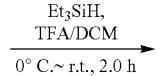

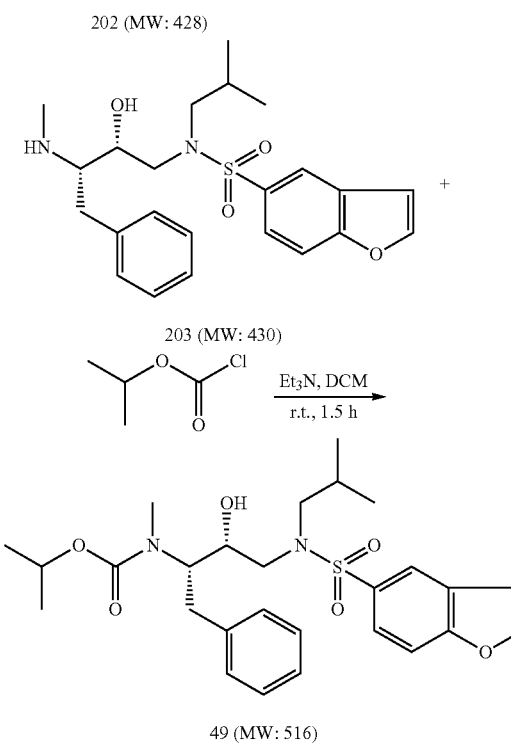

To a solution of 36 (2.20 g, 4.26 mmol) in dichloromethane (6 mL) was added trifluoroacetic acid (3 mL) at 0° C. The mixture was stirred at room temperature for 30 min, after which time 20% sodium bicarbonate (20 mL) was added. The two phases were separated and the aqueous layer was extracted three times with ethyl acetate. The combined organic phase was washed once with brine, dried over anhydrous sodium sulfate and then concentrated in vacuo. The residue was purified on silica gel with ethyl acetate (0-100%) in hexane as eluant to afford 201 as a white solid (1.23 g, 72%).

A solution of 201 (125 mg, 0.3 mmol, 1.0 equiv.), p-toluenesulfonic acid (19 mg, 0.1 mmol, 0.33 equiv.), and 37% aqueous formaldehyde (112 μL, 1.5 mmol, 5.0 equiv.) in THF (3 mL) was stirred at room temperature for 3 h, then diluted with ethyl acetate (15 mL). The solution was washed with 5% sodium bicarbonate once and brine once, then dried over anhydrous sodium sulfate, and concentrated to an oil in vacuo. The crude product 202 was used directly in the next step.

To a solution of 202 in dichloromethane (2 mL) at 0° C. was added trifluoroacetic acid (2 mL) and triethylsilane (0.2 mL). The mixture was stirred at room temperature for 2 h and then quenched with saturated sodium bicarbonate. This solution was extracted three times with ethyl acetate. The combined organic phase was dried over anhydrous sodium sulfate and concentrated to dryness. The crude product 203 was used directly in the next step.

To a solution of 203 in dichloromethane (3 mL) was added triethylamine (84 μL, 0.6 mmol, 2.0 equiv.) and 1.0 M isopropyl chloroformate solution in toluene (0.45 mL, 0.45 mmol, 1.5 equiv.). The mixture was stirred at room temperature for 1.5 h and then the solution was mixed with a small amount of silica gel and evaporated in vacuo to dryness. The residue was purified on silica gel to afford a white solid, 49 (42 mg, 27% overall). MS 517 (MH)$^+$ and 575 (AcOM)$^-$. Purity 99% (HPLC).

Example 2d

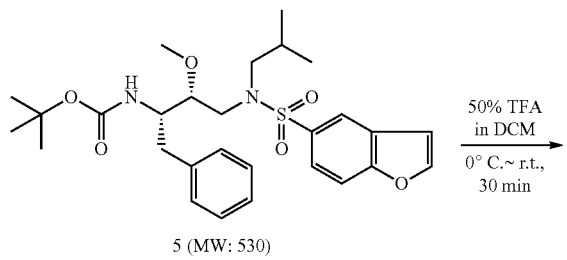

5 (MW: 530)

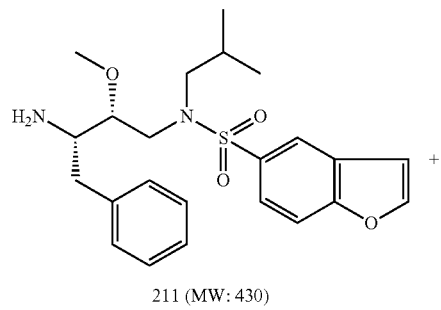

211 (MW: 430)

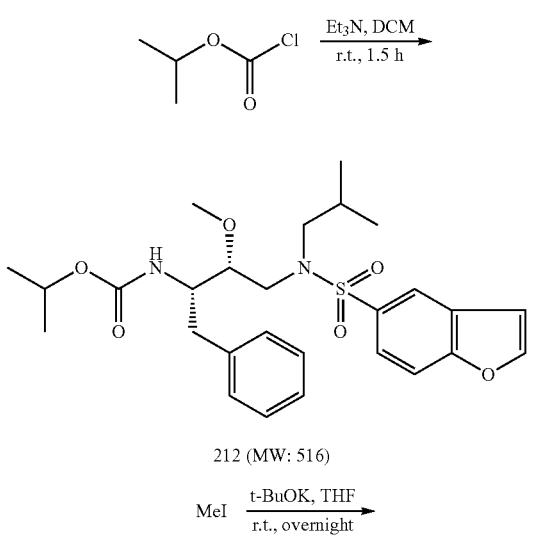

212 (MW: 516)

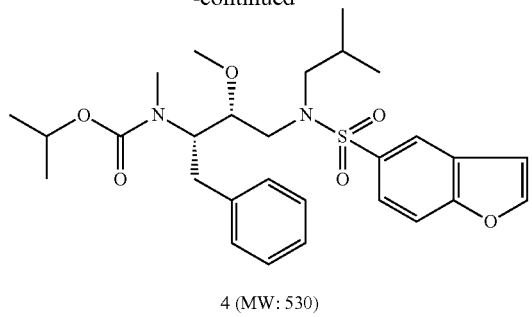

4 (MW: 530)

To a solution of 5 (200 mg, 0.377 mmol) in dichloromethane (1 mL) was added trifluoroacetic acid (0.5 mL) at 0° C. The mixture was stirred at room temperature for 30 min, after which time 20% sodium bicarbonate (10 mL) was added. The phases were separated and aqueous layer extracted three times with ethyl acetate. The combined organic phase was washed once with brine, dried over anhydrous sodium sulfate and then concentrated in vacuo. The crude product (211, 105 mg) was used directly in the next step.

To a solution of 211 in dichloromethane (2 mL) was added triethylamine (68 μL, 0.448 mmol, 2.0 equiv.) and 1.0 M isopropyl chloroformate solution in toluene (0.37 mL, 0.366 mmol, 1.5 equiv.). The mixture was stirred at room temperature for 1.5 h and a small amount of silica gel was added. Then the solution was evaporated to dryness in vacuo. The residue was purified on silica gel (0-40% ethyl acetate in hexane) to afford a white solid, 212 (90 mg, 71%). MS 517 (MH)$^+$ and 575 (AcOM)$^-$. Purity >99% (HPLC).

To a solution of 212 (61 mg, 0.118 mmol, 1.0 equiv.) in THF (1 mL) was added potassium tert-butoxide (53 mg, 0.473 mmol, 4.0 equiv.). After the mixture was stirred at room temperature for 30 min, methyl iodide (29 μL, 0.473 mmol, 4.0 equiv.) was added. The reaction was stirred overnight and then quenched with methanol. The solution was mixed with a small amount of silica gel and concentrated to dryness and the residue was purified on silica gel (0-40% ethyl acetate in hexane) to afford 4 (33 mg, 53%). MS 1083 (2 MNa)$^+$, 531 (MH)$^+$ and 567 (MCl)$^-$. Purity >99% (HPLC).

Example 2e

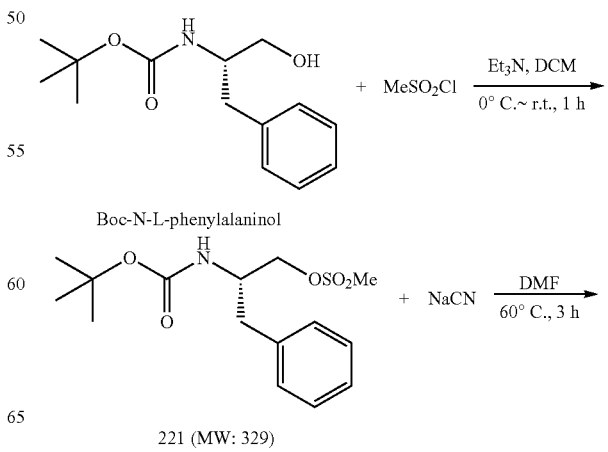

221 (MW: 329)

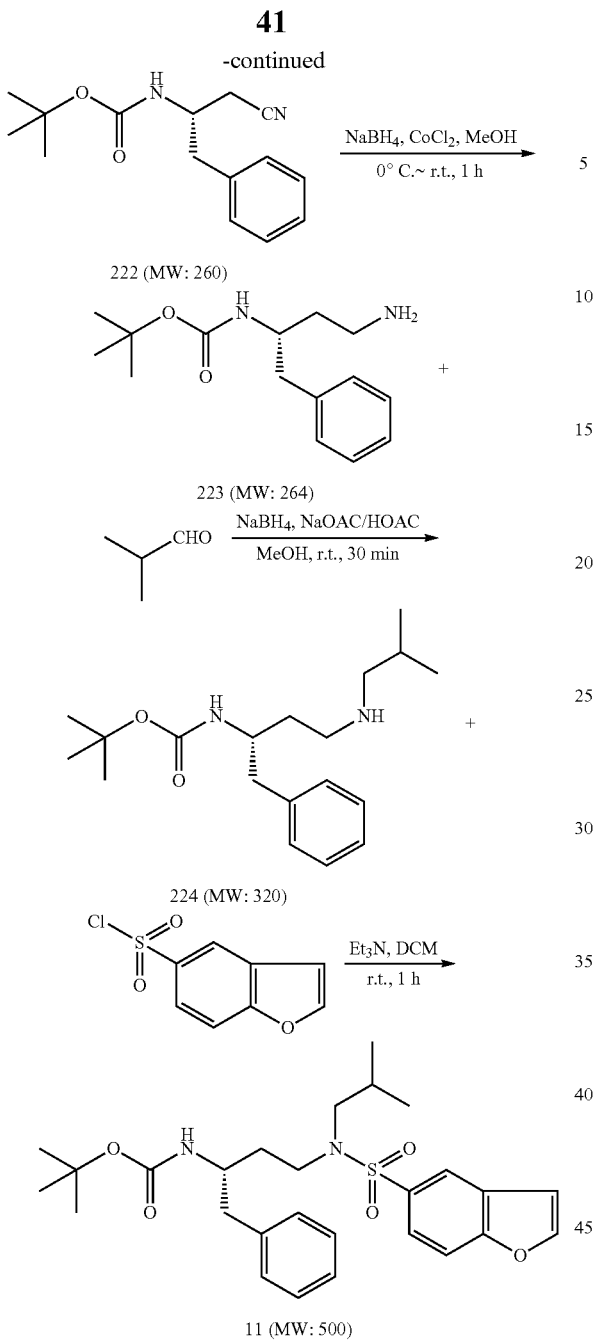

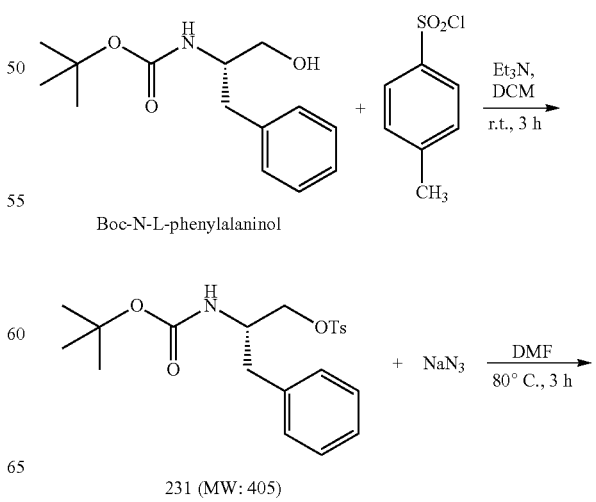

acetate in hexane) on silica gel to afford 222 as a white solid (0.6 g, 23% yield for the two steps). 222 (104 mg, 0.4 mmol, 1.0 equiv.) and cobaltous chloride hexahydrate (190 mg, 0.8 mmol, 2.0 equiv.) were dissolved in methanol and sodium borohydride (151 mg, 4.0 mmol, 10 equiv.) was added in portions with stirring at 0° C. Evolution of hydrogen gas and then a black precipitate was observed during the addition. When the addition was complete, stirring was continued for 1 hour at room temperature. Then the reaction was quenched by the addition of 1.0 M aqueous HCl (6 mL). The mixture was stirred until the black precipitate was dissolved. After the removal of methanol in vacuo and unreacted starting material by extraction with ether, the aqueous layer was made alkaline with concentrated ammonium hydroxide and extracted with ethyl acetate three times. The combined organic phase was washed twice with brine, dried over anhydrous sodium sulfate, and concentrated. Crude 223 (79.4 mg) was used directly in the next step.

To a solution of 223 (79 mg, 0.3 mmol, 1.0 equiv.) in methanol (3 mL) were added sodium acetate (54 mg, 0.66 mmol, 2.2 equiv.), acetic acid (384, 0.66 mmol, 2.2 equiv.) and isobutyraldehyde (60 μL, 0.66 mmol, 2.2 equiv.). The mixture was stirred and treated with sodium borohydride (50 mg, 1.32 mmol, 4.4 equiv.). After the reaction solution was stirred for 30 min at room temperature, 20% aqueous NaHCO$_3$ was added. The reaction mixture was extracted with ethyl acetate three times and the combined organic phase was washed with brine twice, dried over anhydrous sodium sulfate and concentrated in vacuo to afford crude 224 (92 mg), which was used directly in the next step.

To a solution of 224 (45 mg, 0.14 mmol, 1.0 equiv.) in dichloromethane (1.5 mL) was added benzofuran-5-sulfonyl chloride (46 mg, 0.21 mmol, 1.5 equiv.) and triethylamine (39 pt, 0.28 mmol, 2.0 equiv.). The mixture was stirred at room temperature for 1 h and then the solution was mixed with a small amount of silica gel and evaporated in vacuo to dryness. The residue was chromatographed on silica gel to afford 11 as a white solid, (26 mg, 38%). MS 1023 (2 MNa)$^+$, 401 (M-Boc)$^+$ and 559 (AcOM)$^-$. Purity >99% (HPLC).

To an ice-cooled solution of Boc-L-phenylalaminol (2.51 g, 10.0 mmol, 1.0 equiv.) in dichloromethane (40 mL) were added triethylamine (2.1 mL, 15.0 mmol, 1.5 equiv.) and methanesulfonyl chloride (1.2 mL, 15 mmol, 1.5 equiv.). The reaction mixture was stirred for 30 min at 0° C. then 30 min at room temperature. The organic phase was washed consecutively with brine, 1M HCl, brine, 5% aqueous NaHCO3, and brine, dried over anhydrous sodium sulfate and concentrated under reduced pressure to afford the mesylate as a yellow oil (221), which was used directly in the next step.

221 was dissolved in DMF (20 mL), and sodium cyanide (1.2 g, 25 mmol, 2.5 equiv.) was added. The reaction mixture was heated to 60° C. and stirred for 3 h. After cooling to room temperature, water (120 mL) was added and the precipitate was collected and washed with water twice and dried in vacuo overnight. The solid was chromatographed (0-50% ethyl

Example 2f

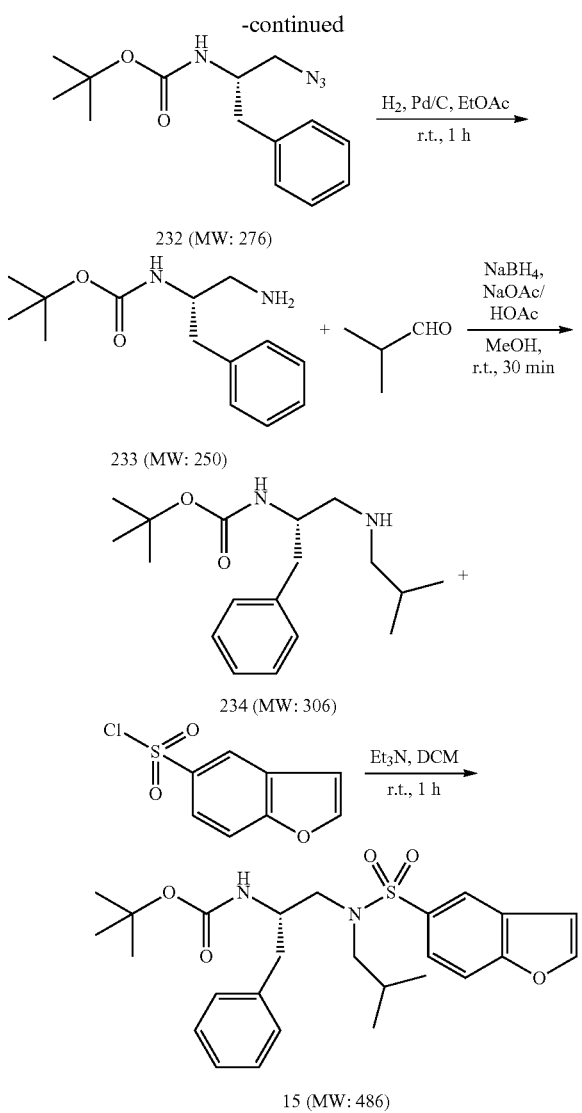

solved in ethyl acetate (3 mL) was hydrogenated at atmospheric pressure for 1 h in the presence of 10% Pd/C (20 mg). The catalyst was removed by filtration through Celite, and the filtrate was concentrated in vacuo to give 233, which was used directly in the next step.

To a solution of 233 in methanol (3 mL) were added sodium acetate (49 mg, 0.60 mmol, 2.0 equiv.), acetic acid (34 µL, 0.60 mmol, 2.0 equiv.) and isobutyraldehyde (55 µL, 0.60 mmol, 2.0 equiv.). The mixture was stirred and treated with sodium borohydride (45 mg, 1.2 mmol, 4.0 equiv.). After 30 min at room temperature, 20% NaHCO$_3$ was added to quench the reaction. The reaction mixture was extracted with ethyl acetate three times and the combined organic phase was washed with brine twice, dried over anhydrous sodium sulfate and concentrated in vacuo to give 234, which was used directly in the next step.

To a solution of 234 in dichloromethane (3 mL) was added benzofuran-5-sulfonyl chloride (97 mg, 0.45 mmol, 1.5 equiv.) and triethylamine (84 µL, 0.60 mmol, 2.0 equiv.). The mixture was stirred at room temperature for 1 h and then the solution was concentrated in vacuo. Preparative TLC (30% ethyl acetate in hexane) afforded 15 as a white solid (14 mg, yield 10% overall). MS 995 (2 MNa)$^+$, 509 (MNa)$^+$, 387 (M-Boc)$^+$, 545 (AcOM)$^-$, and 485 (M-H)$^-$. Purity 97% (HPLC).

Example 2g

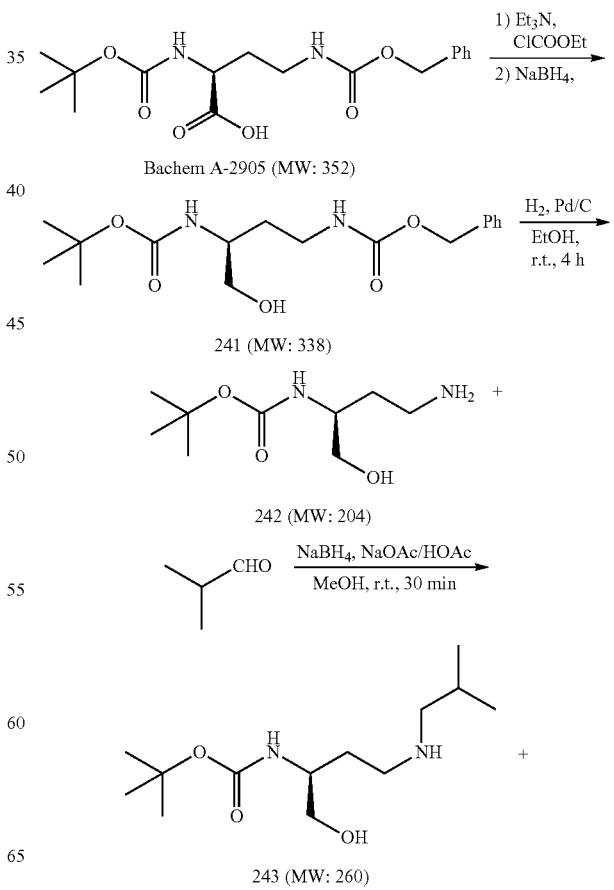

Boc-L-phenylalaminol (1.01 g, 4.0 mmol, 1.0 equiv.) and p-toluenesulfonyl chloride (0.92 g, 4.8 mmol, 1.2 equiv.) were dissolved in dichloromethane (20 mL) and to the solution was added triethylamine (0.84 mL, 6.0 mmol, 1.5 equiv.) at room temperature. The resulting mixture was stirred for 3 h, and then the reaction was quenched with saturated ammonium chloride solution. The phases were separated and the water layer was extracted with ether twice. The combined organic phase was washed once with brine, dried over anhydrous sodium sulfate and concentrated in vacuo. The residue was chromatographed on silica gel (0-20% ethyl acetate in hexane) to afford 231 as a white solid (0.61 g, 38%). Purity 99% (HPLC).

231 (261 mg, 0.64 mmol, 1.0 equiv.) was dissolved in DMF (1.5 mL), and sodium azide (84 mg, 1.28 mmol, 2.0 equiv.) was added. The reaction mixture was heated to 80° C. and stirred for 3 h. After cooling to room temperature, the solution was partitioned between water (5 mL) and ethyl acetate (10 mL). The organic phase was washed with 1N HCl, 5% NaHCO$_3$, and water, dried over anhydrous sodium sulfate and then concentrated in vacuo. The residue was chromatographed on silica gel to afford 232 as a white solid (87 mg, 49%). Purity 99% (HPLC). 232 (87 mg, 0.31 mmol) dis-

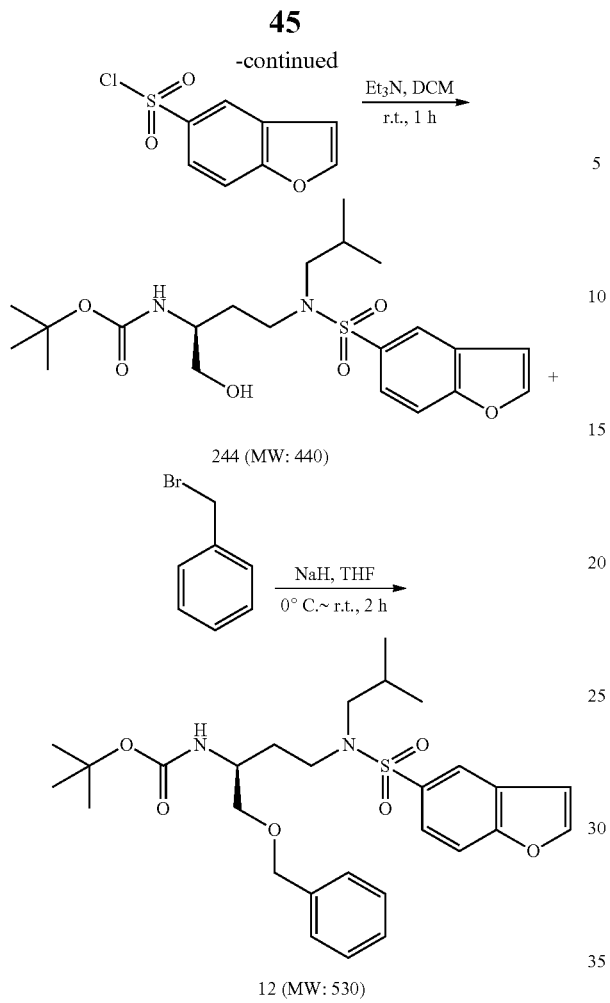

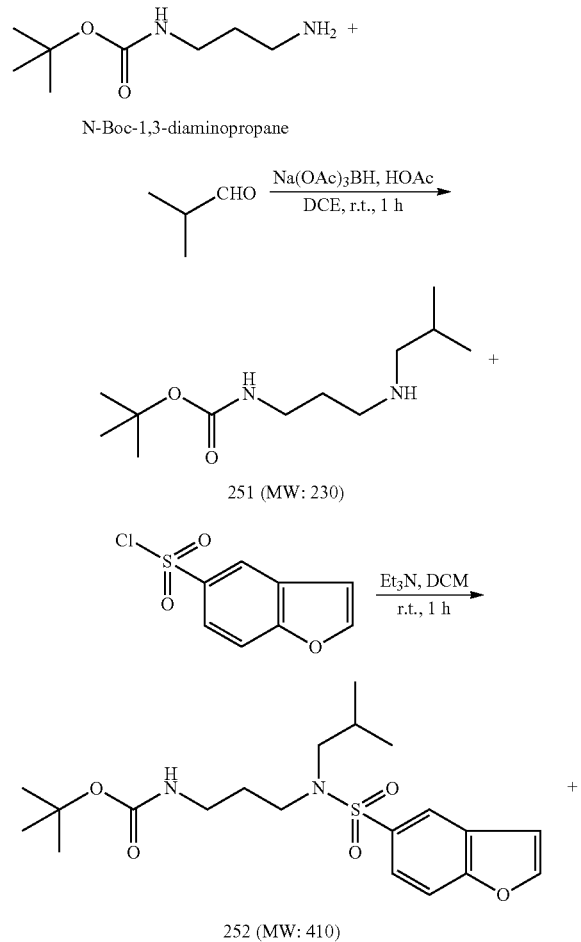

brine twice, dried over anhydrous sodium sulfate and concentrated in vacuo to give 243, which was used directly in the next step.

To a solution of 243 in dichloromethane (2 mL) was added benzofuran-5-sulfonyl chloride (65 mg, 0.30 mmol, 1.5 equiv.) and triethylamine (56 µL, 0.40 mmol, 2.0 equiv.). The mixture was stirred at room temperature for 1 h and then the solution was concentrated in vacuo. The residue was chromatographed on silica gel to afford 244 as a white solid (39 mg, 38% for the three steps). MS 903 (2 MNa)+, 463 (MNa)+, 341 (M-Boc)+ and 499 (AcOM)−. Purity >99% (HPLC).

To a solution of 244 (36 mg, 0.082 mmol, 1.0 equiv.) in THF (1 mL) was added benzyl bromide (39 µL, 0.327 mmol, 4.0 equiv.) and sodium hydride (13 mg, 0.327 mmol, 4.0 equiv.) at 0° C. The mixture was stirred for 2 h while the reaction temperature was allowed to gradually return to ambient temperature. Then the reaction was quenched with methanol. The solution was mixed with a small amount of silica gel and concentrated in vacuo and the residue was chromatographed on silica gel (0-50% ethyl acetate in hexane) to afford a white solid, 12 (22 mg, 51%). MS 1083 (2 MNa)+, 553 (MNa)+, 431 (M-Boc)+ and 589 (MOAc)−. Purity >99% (HPLC).

Example 2h

Boc-L-Dab(Z)—OH.DCHA (534 mg, 1.0 mmol, 1.0 equiv.) was dissolved in THF (6 mL), cooled to 0, and treated with triethylamine (210 µL, 1.5 mmol, 1.5 equiv.) and ethyl chloroformate (114 µL, 1.2 mmol, 1.2 equiv.). The resulting mixture was stirred at 0° C. for 30 min and filtered. The filtrate was added dropwise to a slurry of sodium borohydride (190 mg, 5.0 mmol, 5.0 equiv.) in water (6 mL) at 0° C. After 4 h, the mixture was diluted with brine and extracted with ethyl acetate. The combined organic phase was dried over anhydrous sodium sulfate and concentrated in vacuo. The residue was chromatographed on silica gel using 0-75% ethyl acetate/dichloromethane as eluant to afford 241 as a white solid (170 mg, 50%). Purity 99% (HPLC).

To a solution of 241 (170 mg, 0.5 mmol) in ethanol (5 mL) was added 10% Pd/C (30 mg). A hydrogen balloon was connected to the reaction vessel. After the system was fully flushed with hydrogen, the reaction mixture was stirred at room temperature for 4 h, and then filtered through celite and concentrated in vacuo to give 97 mg of 242, which was used directly in the next step.

To a solution of 242 (45 mg, 0.22 mmol, 1.0 equiv.) in methanol (2 mL) were added sodium acetate (36 mg, 0.44 mmol, 2.0 equiv.), acetic acid (25 µL, 0.44 mmol, 2.0 equiv.) and isobutyraldehyde (40 µL, 0.44 mmol, 2.0 equiv.). The mixture was stirred and treated with sodium borohydride (33 mg, 0.88 mmol, 4.0 equiv.). After the reaction solution was stirred for 30 min at room temperature, 20% NaHCO3 was added. The reaction mixture was extracted with ethyl acetate three times and the combined organic phase was washed with Example 2i

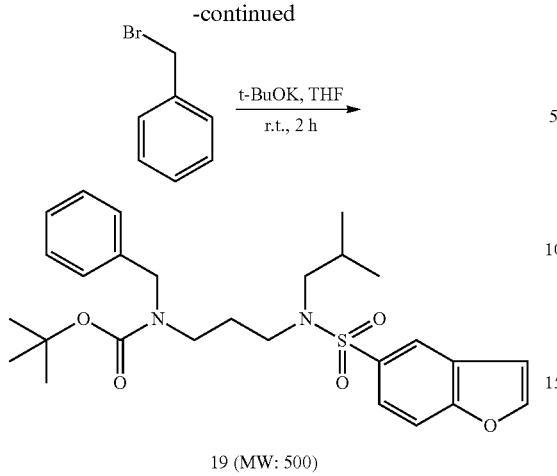

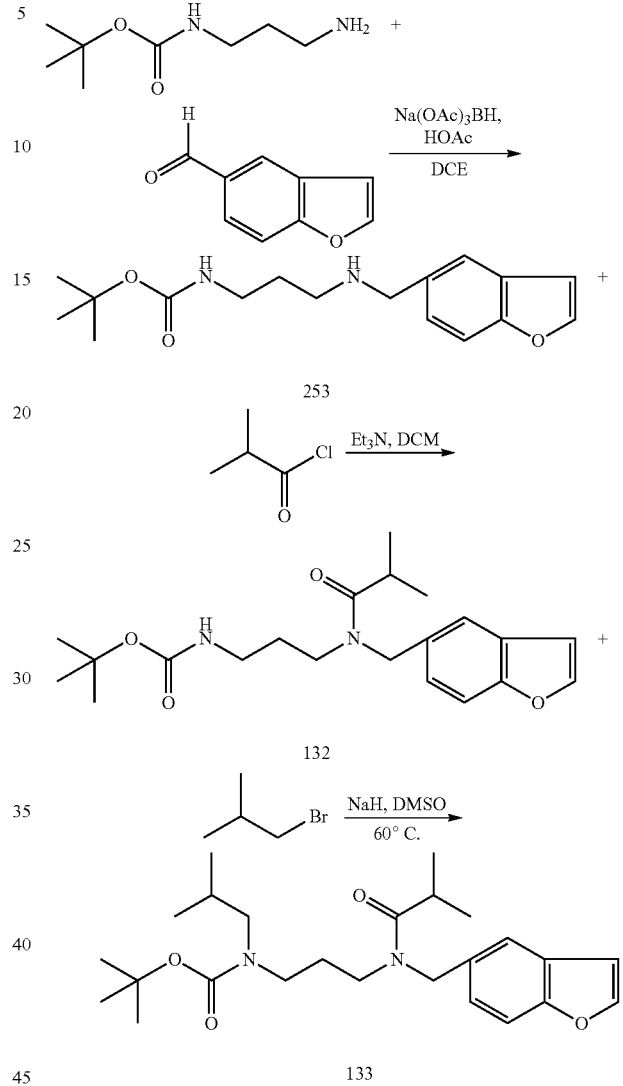

To a solution of N-Boc-1,3-diaminopropane (6.97 g, 40 mmol, 1.0 equiv.) in anhydrous 1,2-dichloroethane (160 mL) was added isobutyraldehyde (3.03 g, 42 mmol, 1.05 equiv.) and acetic acid (2.3 mL, 40 mmol, 1.0 equiv.). The solution was stirred for 10 min, and then was treated with sodium triacetoxyborohydride (12.72 g, 60 mmol, 1.5 equiv.). The resulting mixture was stirred for 1 h and then the reaction was quenched with 20% aqueous NaHCO$_3$ (100 mL) and ethyl acetate (200 mL). The layers were separated and the organic phase was washed twice with brine, dried over anhydrous Na$_2$SO$_4$, and concentrated in vacuo to afford crude 251, which was used directly in the next step.

To a solution of 251 (40 mmol, 1.0 equiv.) in dichloromethane (200 mL) was added benzofuran-5-sulfonyl chloride (10.4 g, 48 mmol, 1.2 equiv.) and triethylamine (8.4 mL, 60 mmol, 1.5 equiv.). The mixture was stirred at room temperature for 2 h and then the reaction was quenched by the addition of 1M HCl solution (100 mL) and ethyl acetate (200 mL). The two phases was separated and the organic layer was washed with brine twice, dried over anhydrous Na$_2$SO$_4$, and concentrated in vacuo. The residue was purified on silica gel with ethyl acetate/hexane (1/3) as eluant to afford a colorless oil, 252 (5.62 g, 34% overall). MS 433 (MNa)$^+$, 311 (M-Boc)$^+$ and 469 (AcOM)$^-$. Purity >99% (HPLC).

To a solution of 252 (5.6 g, 13.7 mmol, 1.0 equiv) in anhydrous THF (70 mL) was added potassium tert-butoxide (3.07 g, 27.3 mmol, 2.0 equiv.) immediately followed by benzyl bromide (2.4 mL, 20.5 mmol, 1.5 equiv.). The resulting mixture was stirred at room temperature for 1 h, after which time the reaction was quenched by the addition of 1M HCl solution and ether. The two phases were separated and the water layer was extracted twice with ether. The combined organic phase was washed twice with brine, dried over anhydrous Na$_2$SO$_4$ and concentrated in vacuo. The residue was purified on silica gel with ethyl acetate/hexane (1/6) as eluant to afford 19 as a colorless oil (6.5 g, 95%). $^1$H NMR (δ, CDCl$_3$): 8.19 (s, 1H), 7.86 (s, 1H), 7.81 (d, J=8.7 Hz, 1H), 7.69 (d, J=8.7 Hz, 1H), 7.22-7.45 (m, 5H), 6.98 (s, 1H), 4.50 (s, 2H), 3.05-3.30 (m, 4H), 2.96 (d, J=7.4 Hz, 2H), 1.75-1.94 (m, 3H), 1.55 (s, 9H), 0.99 (d, j=6.6 Hz, 6H). MS 523 (Ma)$^+$, and 401 (M-Boc). Purity >99% (HPLC).

To a solution of benzofuran-5-carbaldehyde (146 mg, 1.0 mmol, 1.0 equiv.) in anhydrous 1,2-dichloroethane (5 mL) was added N-Boc-1,3-diaminopropane (192 μL, 1.1 mmol, 1.1 equiv.) and acetic acid (57 μL, 1.0 mmol, 1.0 equiv.). The solution was stirred for 10 min, and then was treated with sodium triacetoxyborohydride (297 mg, 1.4 mmol, 1.4 equiv.). The resulting mixture was stirred for 3 h at room temperature and then the reaction was quenched with the addition of saturated aqueous NaHCO$_3$ solution. The aqueous layer was extracted with ethyl acetate three times and the combined organic phase was washed twice with brine, dried over anhydrous Na$_2$SO$_4$, and concentrated in vacuo to afford crude 253 (287 mg), which was used directly in the next step.

To a solution of 253 (96 mg, 0.32 mmol, 1.0 equiv.) in dichloromethane (1 mL) was added isobutyryl chloride (34 μL, 0.32 mmol, 1.0 equiv.) and triethylamine (49 μL, 0.35 mmol, 1.1 equiv.). The mixture was stirred at room temperature for 1 h and then the reaction solution was transferred via syringe onto a preparative silica gel TLC plate. The plate was eluted with 1:3 ethyl acetate/hexane to give 105 mg (88%)

132, MS 771 (2 MNa)⁺, 397 (MNa)⁺, 375 (MH)⁺, 275 (M-Boc)⁺. HPLC purity >99%.

132 (38 mg, 0.1 mmol, 1.0 equiv) and sodium hydride (60% dispersion in mineral oil, 8 mg, 0.2 mmol, 2.0 equiv.) were dissolved in anhydrous DMSO (0.5 mL). The solution was stirred at room temperature for 5 min and then was treated with isobutyl bromide (24 µL, 0.22 mmol, 2.2 equiv.). The mixture was heated to 60° C. and stirred for 1.5 h and then returned to room temperature. An additional portion of sodium hydride (8 mg, 0.2 mmol, 2.0 equiv.) was introduced and 5 minutes later an additional portion of isobutyl bromide (24 µL, 0.22 mmol, 2.2 equiv.). The resulting mixture was heated to 60° C. and stirred for an additional 1.5 h and the reaction then quenched with methanol. The final solution was transferred via syringe onto a preparative silica gel TLC plate. The plate was eluted with 1:4 ethyl acetate/hexane to give 15 mg (35%) 133. MS 883 (2 MNa)⁺, 453 (MNa) % 431 (MH)⁺ and 331 (M-Boc)⁺. HPLC purity >99%.

Example 2j

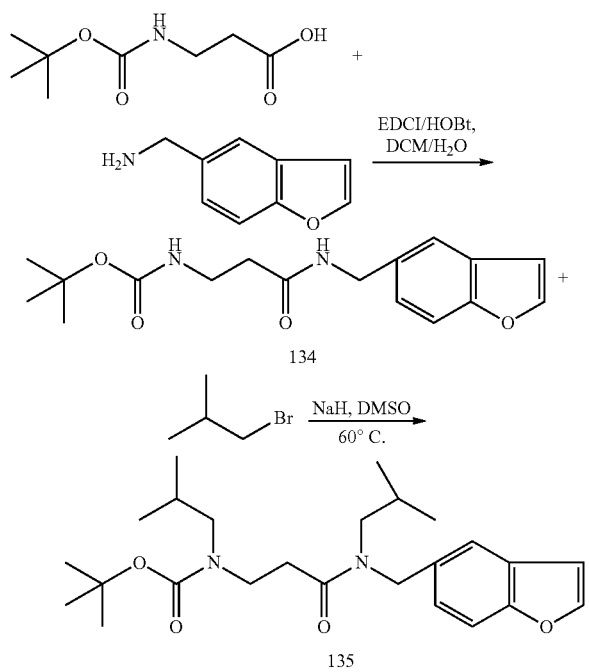

To a solution of benzofuran-5-ylmethylamine (147 mg, 1.0 mmol, 1.0 equiv.) in dichloromethane (10 mL) were added sequentially water (10 mL), Boc-β-Ala-OH (208 mg, 1.1 mmol, 1.1 equiv.) and HOBT (149 mg, 1.1 mmol, 1.1 equiv.). The mixture was then cooled in an ice bath to 0-5° C., and N-(3-Dimethylaminopropyl)-N'-ethylcarbodiimide hydrochloride (EDCI) (211 mg, 1.1 mmol, 1.1 equiv.) was added. The resulting mixture was then stirred overnight at room temperature. The reaction was quenched with saturated aqueous NaHCO₃ solution. The aqueous phase was extracted with ethyl acetate three times and the combined organic phase was dried over anhydrous Na₂SO₄, and concentrated in vacuo. The residue was purified using medium pressure chromatography (ethyl acetate/hexane gradient, 0-100%) to afford 258 mg (81%) 134 as a white solid, MS 659 (2 MNa)⁺, 341 (MNa)⁺, 319 (MH)⁺, and 377. HPLC purity >99%.

134 (48 mg, 0.15 mmol, 1.0 equiv) and sodium hydride (60% dispersion in mineral oil, 12 mg, 0.3 mmol, 2.0 equiv.) were added to anhydrous DMSO (0.7 mL). The solution was stirred at room temperature for 10 min and then treated with isobutyl bromide (33 µL 0.30 mmol, 2.0 equiv.). The mixture was then heated to 60° C. and stirred for 1 h and then returned to room temperature. An additional portion of sodium hydride (12 mg, 0.3 mmol, 2.0 equiv.) was introduced and 5 minutes later an additional portion of isobutyl bromide (33 µL, 0.30 mmol, 2.0 equiv.). The resulting mixture was heated to 60° C. and stirred for 1 h and then returned to room temperature and quenched with methanol. The final solution was transferred onto a preparative silica gel TLC plate via syringe. The plate was eluted with 1:3 ethyl acetate/hexane to give 3.0 mg 135 (5%). MS 883 (2 MNa)⁺, 453 (MNa)⁺, 431 (MH)⁺ and 331 (M-Boc)⁺. HPLC purity >99%.

Variations, modifications, and other implementations of what is described herein will occur to those of ordinary skill in the art without departing from the spirit and the scope of the technology. Accordingly, the technology is not to be limited only to the preceding illustrative descriptions.

What is claimed is:

1. A composition comprising a compound of formula I and a compound of formula II in an amount effective to treat a disease or disorder:

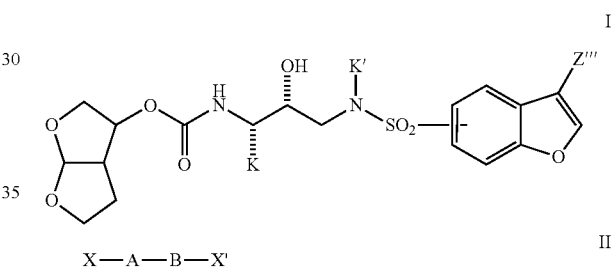

wherein:
K is aralkyl optionally substituted with one or more groups selected from alkyl, halo, nitro, cyano, CF₃, C₃-C₇ cycloalkyl, C5-C7 cycloalkenyl, R6, OR2, SR2, NHR2, OR3, SR3, NHR3, OR6, SR6, or NHR6;

K' is alkyl;

Z''' is C₁-C₆ alkyl substituted with N(R)CO$_n$R;

X is selected from the group consisting of alkyl, aryl, aralkyl, heteroaryl, and heteroaralkyl, wherein X contains from 1 to 12 carbon atoms and, when X is heteroaryl or heteroaralkyl, X contains from 1 to 3 heteroatoms independently selected from the group consisting of O, S, and N, A is —OCON(R2)—, —S(O)$_n$N(R2)—, —CON(R2)—, —COCO(NR2)—, —N(R2)CON(R2)—, —N(R2)S(O)$_n$N(R2)—, N(R2)CO or —N(R2)COO—;

B is —(CG₁G₂)$_m$—, wherein m is 2-6 and wherein G₁ and G₂ are the same or different and wherein each G₁ and G₂ independently is selected from the group consisting of a bond, H, halo, haloalkyl, OR, optionally substituted alkyl, optionally substituted alkenyl, optionally substituted alkynyl, optionally substituted aryl, optionally substituted cycloalkyl, optionally substituted cycloalkylalkyl, optionally substituted aralkyl, optionally substituted heteroaryl, and optionally substituted heterocycloalkyl wherein each optional substitution independently is selected from the group consisting of alkyl, halo, cyano, CF₃, OR, $C_3$-$C_7$ cycloalkyl, $C_5$-$C_7$ cycloalkenyl, R6, OR2, SR2, $N(R2)_2$, OR3, SR3, NR2R3, OR6, SR6, and NR2R6, and wherein $G_1$ and $G_2$, together with the atoms to which they are attached, optionally may form a 3-7-membered carbocyclic or heterocyclic ring containing up to three heteroatoms selected from the group consisting of N, S and O, and wherein said ring optionally may be substituted with up to 3 R7 moieties, X' is

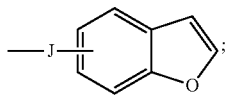

wherein J is selected from:
—N(D)-$SO_n$—, —N(D)-$CO_n$—, —N(D)-(R8)$_q$—, —N(CO-D)-(R8)$_q$—, —N($SO_n$-D)-(R8)$_q$—, —$SO_n$—N(D)-(R8)$_q$—, or —$CO_n$—N(D)-(R8)$_q$—, wherein D is selected from hydrogen, alkyl, alkenyl, alkynyl, cycloalkyl, cycloalkylalkyl, heterocycloalkyl, heterocycloalkylalkyl, aryl, heteroaryl, heteroaralkyl or aralkyl, O-alkyl, O-cycloalkyl, O-cycloalkylalkyl, O-heterocycloalkyl, O-heterocycloalkylalkyl, O-heteroaralkyl O-aralkyl, N(R2)-alkyl, N(R2)-cycloalkyl, N(R2)-cycloalkylalkyl, N(R2)-heterocycloalkyl, N(R2)-heterocycloalkylalkyl, N(R2)-heteroaralkyl, N(R2)-aralkyl, wherein D optionally is substituted by alkyl, halo, nitro, cyano, O-alkyl, or S-alkyl;

wherein R is H, alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein each R2 is independently selected from the group consisting of H, $C_1$-$C_{12}$ alkyl, $C_3$-$C_8$ cycloalkyl, aryl, aralkyl, heteroaryl, heteroaralkyl, and heterocycloalkyl each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_n$R, $CON(R)_2$, C(S)R, $C(S)N(R)_2$, $SO_nN(R)_2$, SR, $SO_nR$, $N(R)_2$, $N(R)CO_nR$, $NRS(O)_nR$, NRC[=N(R)]N(R)$_2$, $N(R)N(R)CO_nR$, $NRPO_nN(R)_2$, $NRPO_nOR$, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

or each R2 is independently selected from the group consisting of $C_1$-$C_6$ alkyl; substituted by aryl or heteroaryl; which groups optionally are substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, NRC[=N(R)]N(R)$_2$, N(R)N(R)CO$_n$R, NRPO$_n$N(R)$_2$, NRPO$_n$OR;

R3 is $C_2$-$C_6$ alkenyl, $C_2$-$C_6$ alkynyl, $C_3$-$C_8$ cycloalkyl, $C_5$-$C_8$ cycloalkenyl, or heterocyclo; which groups optionally are substituted with one or more substituents selected from the group consisting of halo, OR2, R2-OH, R2-halo, $NO_2$, CN, $CO_n$R2, $C(O)N(R2)_2$, $C(O)N(R2)N(R2)_2$, $C(S)R2$, $C(S)N(R2)_2$, $S(O)_nN(R2)_2$, SR2, $SO_nR2$, $N(R)_2$, $N(R2)CO_nR2$, NR2S(O)$_n$R2, NR2CP[=(R2)]N(R2)$_2$, N(R2)N(R2)CO$_n$R2, oxo, =N—OR2, =N—N(R2)$_2$, =NR2, =NNRC(O)N(R2)$_2$, =NNR2C(O)$_n$R2, =NNR2S(O)$_n$N(R2)$_2$, and =NNR2S(O)$_n$(R2);

R6 is aryl or heteroaryl, wherein said aryl or heteroaryl optionally are substituted with one or more groups selected from the group consisting of aryl, heteroaryl, R2, R3, halo, OR2, R2OH, R2-halo, $NO_2$, CN, $CO_n$R2, $C(O)N(R2)_2$, $C(O)N(R2)N(R2)_2$, $C(S)R2$, $C(S)N(R2)_2$, $S(O)_nN(R2)_2$, SR2, $SO_nR2$, $N(R)_2$, $N(R2)CO_nR2$, NR2S(O)$_n$R2, NR2C[=(R2)]N(R2)$_2$, N(R2)N(R2)CO$_n$R2, OC(O)R2, OC(S)R2, OC(O)N(R2)$_2$, and OC(S)N(R2)$_2$;

R7 is H, oxo, $C_1$-$C_{12}$ alkyl; $C_3$-$C_8$ cycloalkyl, aryl, aralkyl, heteroaryl, heteroaralkyl, or heterocycloalkyl, each further optionally substituted with one or more substituents selected from the group consisting of $C_2$-$C_6$ alkenyl, $C_2$-$C_6$ alkynyl, $C_3$-$C_8$ cycloalkyl, $C_5$-$C_8$ cycloalkenyl, heterocyclo; halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, NRC[=(R)]N(R)$_2$, $N(R)N(R)CO_nR$, $NRPO_nN(R)_2$, $NRPO_nOR$, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

R8 is alkyl, haloalkyl, alkenyl, alkynyl, alkoxyalkyl, cycloalkyl, cycloalkylalkyl, heterocycloalkyl, heteroaryl, heterocycloalkylalkyl, aryl, aralkyl, and heteroaralkyl;

wherein n=1-2, and
wherein q=0-1, provided that: when X is a 5-7 membered non-aromatic monocyclic heterocycle, optionally fused or bridged with one or more 3-7 membered non-aromatic monocyclic heterocycle to form a polycyclic system, wherein any of said heterocyclic ring systems contains one or more heteroatoms selected from O, N, S, and P, and when B is

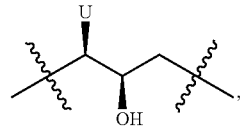

wherein U is selected from optionally substituted alkyl, optionally substituted alkenyl, optionally substituted alkynyl, optionally substituted aryl, optionally substituted cycloalkyl, or optionally substituted aralkyl, then J cannot be —N(D)-$SO_n$— or —N(D)-$CO_n$—.

2. The composition according to claim 1, wherein X optionally is substituted with one or more substituents selected from the group consisting of halo, OR, ROH, R-halo, CN, $CO_nR$, $CON(R)_2$, $SO_nN(R)_2$, SR, $SO_nR$, $N(R)_2$, $N(R)CO_nR$, $NRS(O)_nR$, oxo, and =N—OR.

3. The composition according to claim 1, wherein $G_1$ and $G_2$ are the same or different and independently are selected from the group consisting of a bond, H, OR, optionally substituted alkyl, optionally substituted aryl, optionally substituted cycloalkyl, optionally substituted cycloalkylalkyl, optionally substituted aralkyl, optionally substituted heteroaryl, and optionally substituted heteroaralkyl.

4. The composition according to claim 1, wherein $G_1$ and $G_2$ do not form a ring.

5. The composition according to claim 1, wherein at least one $G_1$ and at least one $G_2$ form a ring.

6. The composition according to claim 1, wherein $G_1$ and $G_2$ are different.

7. The composition according to claim 1, wherein neither $G_1$ nor $G_2$ is OH.

8. The composition according to claim 1, wherein G1 and G2 are selected from the group consisting of H, O-alkyl, alkyl, optionally substituted aryl and optionally substituted aralkyl.

9. The composition according to claim 1, wherein J is

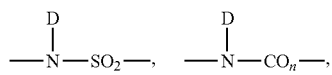

—N(D)-(R8)$_q$—, —SOn-N(D)-(R8)$_q$— or —COn-N(D)-(R8)$_q$—.

10. The composition according to claim 1, wherein D is selected from the group consisting of hydrogen, alkyl, cycloalkyl, cycloalkylalkyl, aryl, heteroaryl, heteroaralkyl and aralkyl, wherein D optionally is substituted by alkyl, halo, nitro, cyano, O-alkyl, or S-alkyl.

11. The composition according to claim 1, wherein K is benzyl, and K' is isobutyl.

12. The composition according to claim 1, wherein the compound of formula I is

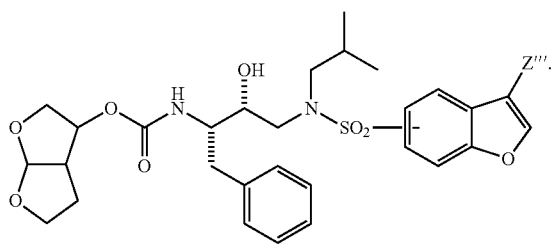

13. The composition according to claim 1, wherein the compound of formula II is

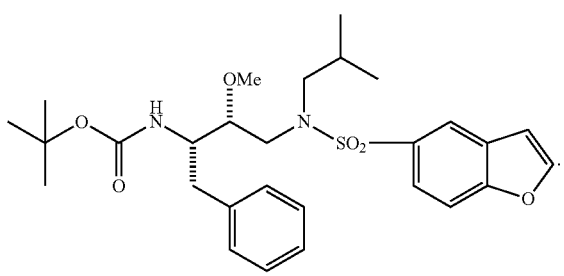 [SMILES: CO[C@H](CN(CC(C)C)S(=O)(=O)c1ccc2occc2c1)[C@H](Cc1ccccc1)NC(=O)OC(C)(C)C]

14. The composition according to claim 1, wherein the compound of formula I is

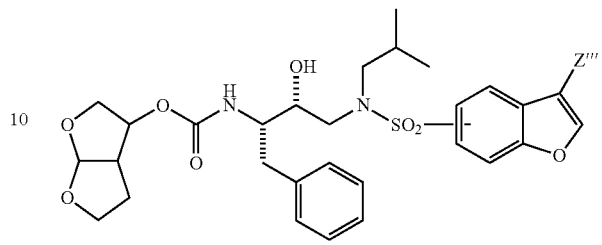

and the compound of formula II is

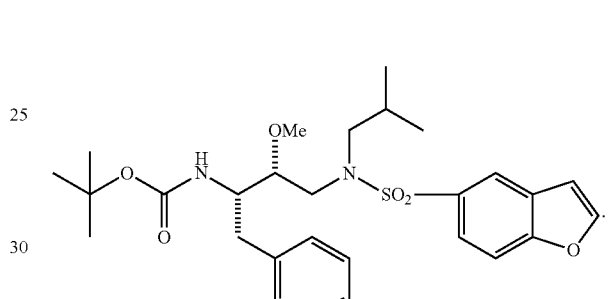

15. The composition according to claim 14, wherein Z''' is —CH$_2$—N(R)CO$_n$R, —CH$_2$—NHCO$_n$R or —CH$_2$—NHCO$_2$Et.

16. The composition according to claim 1, further comprising an antiretroviral agent other than a compound of formula II.

17. A method of treating a disease associated with a viral infection, comprising administering to a subject suffering from said disease an effective amount of a composition according to claim 1.

18. The method according to claim 17 wherein said disease is an HIV infection.

* * * * *

UNITED STATES PATENT AND TRADEMARK OFFICE
CERTIFICATE OF CORRECTION

PATENT NO. : 8,673,970 B2  
APPLICATION NO. : 12/919011  
DATED : March 18, 2014  
INVENTOR(S) : Eissenstat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 402 days.

Signed and Sealed this

Twenty-ninth Day of September, 2015

Michelle K. Lee  
*Director of the United States Patent and Trademark Office*